US012295772B2

(12) United States Patent
Wollowick et al.

(10) Patent No.: US 12,295,772 B2
(45) Date of Patent: *May 13, 2025

(54) SYSTEMS AND METHODS FOR INTRA-OPERATIVE IMAGE ANALYSIS

(71) Applicant: DePuy Synthes Products, Inc., Raynham, MA (US)

(72) Inventors: Noah D. Wollowick, Westport, CT (US); Andrew J. Cooper, Largo, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/611,186

(22) Filed: Mar. 20, 2024

(65) Prior Publication Data
US 2024/0245375 A1 Jul. 25, 2024

Related U.S. Application Data

(63) Continuation of application No. 16/938,912, filed on Jul. 24, 2020, now abandoned, which is a (Continued)

(51) Int. Cl.
A61B 6/50 (2024.01)
A61B 6/00 (2024.01)
(Continued)

(52) U.S. Cl.
CPC ............... A61B 6/505 (2013.01); A61B 6/12 (2013.01); A61B 6/5235 (2013.01); A61B 34/10 (2016.02);
(Continued)

(58) Field of Classification Search
None
See application file for complete search history.

(56) References Cited

U.S. PATENT DOCUMENTS 5,715,836 A  2/1998 Kliegis et al.
6,205,411 B1  3/2001 DiGioia, III et al.
(Continued)

FOREIGN PATENT DOCUMENTS

CN 104244860 A 12/2014
EP 1188421 A2 3/2002
(Continued)

OTHER PUBLICATIONS

Bachhal et al., "A new method of measuring acetabular cup anteversion on simulated radiographs," International Orthopaedics (SICOT), May 31, 2012, pp. 1813-1818, vol. 36, Springer.
(Continued)

Primary Examiner — Christopher Koharski
Assistant Examiner — Farouk A Bruce
(74) Attorney, Agent, or Firm — Barnes & Thornburg LLP

(57) ABSTRACT

A system and method that acquire (i) at least a reference image including one of a preoperative image of a surgical site with skeletal and articulating bones and a contralateral image on an opposite side of the patient from the surgical site and (ii) at least an intraoperative image of the site after an implant has been affixed to the articulating bone. The system generates at least one reference landmark point on at least one anatomical feature on the articulating bone in the reference image and at least one intraoperative landmark point on that anatomical feature in the intraoperative image. The reference and intraoperative images are compared and differences between the orientation of the articulating bone in the two images are utilized to analyze at least one of offset and length differential.

20 Claims, 22 Drawing Sheets

Related U.S. Application Data continuation of application No. 14/995,057, filed on Jan. 13, 2016, now Pat. No. 10,765,384, which is a continuation-in-part of application No. 14/630,300, filed on Feb. 24, 2015, now Pat. No. 10,758,198.

(60) Provisional application No. 62/105,183, filed on Jan. 19, 2015, provisional application No. 62/080,953, filed on Nov. 17, 2014, provisional application No. 62/051,238, filed on Sep. 16, 2014, provisional application No. 62/016,483, filed on Jun. 24, 2014, provisional application No. 61/980,659, filed on Apr. 17, 2014, provisional application No. 61/948,534, filed on Mar. 5, 2014, provisional application No. 61/944,520, filed on Feb. 25, 2014.

(51) Int. Cl.
*A61B 6/12* (2006.01)
*A61B 6/46* (2024.01)
*A61B 34/10* (2016.01)
*A61B 34/20* (2016.01)
*G06T 7/00* (2017.01)
*G06T 7/33* (2017.01)

(52) U.S. Cl.
CPC .............. *G06T 7/0014* (2013.01); *G06T 7/33* (2017.01); *A61B 6/463* (2013.01); *A61B 2034/108* (2016.02); *A61B 2034/2068* (2016.02); *G06T 2207/10116* (2013.01); *G06T 2207/30008* (2013.01); *G06T 2207/30052* (2013.01)

(56) References Cited

U.S. PATENT DOCUMENTS

| | | | |
|---|---|---|---|
| 6,597,818 B2 | 7/2003 | Kumar et al. |
| 6,614,453 B1 | 9/2003 | Suri et al. |
| 8,249,318 B2 | 8/2012 | Schmitt et al. |
| 8,311,791 B1 | 11/2012 | Avisar |
| 8,484,001 B2 | 7/2013 | Glozman et al. |
| 8,635,082 B2 | 1/2014 | Woods et al. |
| 8,831,324 B2 | 9/2014 | Penenberg |
| 8,861,818 B2 | 10/2014 | Ito |
| 8,917,290 B2 | 12/2014 | Beck |
| 9,603,711 B2 | 3/2017 | Bojarski et al. |
| 10,182,871 B2 | 1/2019 | Wollowick et al. |
| 10,433,914 B2 | 10/2019 | Wollowick et al. |
| 10,610,305 B2 | 4/2020 | Wollowick et al. |
| 10,733,914 B2 | 8/2020 | Kruchko |
| 10,758,198 B2 | 9/2020 | Wollowick et al. |
| 10,765,384 B2 | 9/2020 | Wollowick et al. |
| 10,959,782 B2 | 3/2021 | Wollowick et al. |
| 11,318,025 B2 | 5/2022 | Schipper et al. |
| 11,534,127 B2 | 12/2022 | Wollowick et al. |
| 11,642,174 B2 | 5/2023 | Wollowick et al. |
| 11,887,306 B2 | 1/2024 | Cooper et al. |
| 2002/0055692 A1 | 5/2002 | Tanaka et al. |
| 2003/0176860 A1 | 9/2003 | Shimura |
| 2004/0087852 A1 | 5/2004 | Chen et al. |
| 2004/0171924 A1 | 9/2004 | Mire et al. |
| 2005/0015005 A1 | 1/2005 | Kockro |
| 2005/0054917 A1 | 3/2005 | Kitson |
| 2005/0203384 A1 | 9/2005 | Sati et al. |
| 2006/0095047 A1 | 5/2006 | de la Barrera |
| 2006/0293614 A1 | 12/2006 | Radinsky et al. |
| 2007/0015999 A1 | 1/2007 | Heldreth et al. |
| 2007/0066917 A1 | 3/2007 | Hodorek et al. |
| 2007/0078678 A1 | 4/2007 | DiSilvestro et al. |
| 2008/0021299 A1 | 1/2008 | Meulink |
| 2008/0056552 A1 | 3/2008 | Muller |
| 2008/0075348 A1 | 3/2008 | Rappaport et al. |
| 2008/0101682 A1 | 5/2008 | Blandford et al. |
| 2008/0120262 A1 | 5/2008 | Habets et al. |
| 2008/0146969 A1* | 6/2008 | Kurtz ................ A61B 17/56 600/595 |
| 2008/0161680 A1 | 7/2008 | von Jako et al. |
| 2008/0255584 A1 | 10/2008 | Beverland et al. |
| 2009/0216230 A1 | 8/2009 | Pizarro |
| 2009/0234217 A1 | 9/2009 | Mire et al. |
| 2009/0089034 A1 | 12/2009 | Dardenne et al. |
| 2010/0030231 A1 | 2/2010 | Revie et al. |
| 2010/0086181 A1 | 4/2010 | Zug et al. |
| 2010/0198351 A1 | 8/2010 | Meulink |
| 2010/0249507 A1 | 9/2010 | Prisco et al. |
| 2010/0250571 A1 | 9/2010 | Pierce |
| 2010/0256479 A1 | 10/2010 | Park et al. |
| 2011/0012905 A1 | 1/2011 | Kawahara |
| 2011/0082367 A1 | 4/2011 | Regazzoni |
| 2011/0093087 A1 | 4/2011 | Mcmahon et al. |
| 2011/0214279 A1 | 9/2011 | Park et al. |
| 2011/0268325 A1 | 11/2011 | Teichman et al. |
| 2011/0313424 A1 | 12/2011 | Bono et al. |
| 2011/0319941 A1 | 12/2011 | Bar et al. |
| 2012/0016269 A1 | 1/2012 | Moctezuma de la Barrera |
| 2012/0141034 A1 | 6/2012 | Iannotti et al. |
| 2012/0157887 A1 | 6/2012 | Fanson et al. |
| 2012/0194505 A1 | 8/2012 | Beck |
| 2012/0194666 A1 | 8/2012 | Jackson |
| 2012/0209394 A1 | 8/2012 | Bojarski et al. |
| 2012/0230573 A1 | 9/2012 | Ito et al. |
| 2013/0046310 A1 | 2/2013 | Ranawat et al. |
| 2013/0053858 A1 | 2/2013 | Penenberg |
| 2013/0053859 A1 | 2/2013 | Penenberg |
| 2013/0060146 A1 | 3/2013 | Yang et al. |
| 2013/0072821 A1 | 3/2013 | Odermatt et al. |
| 2013/0135721 A1 | 5/2013 | An et al. |
| 2013/0190887 A1 | 7/2013 | Fanson et al. |
| 2013/0197687 A1 | 8/2013 | Pavlovskaia et al. |
| 2013/0296078 A1 | 11/2013 | Solheim et al. |
| 2013/0304429 A1 | 11/2013 | Haimerl |
| 2014/0003700 A1 | 1/2014 | Hermosillo Valadez et al. |
| 2014/0062863 A1 | 3/2014 | Yu et al. |
| 2014/0073907 A1 | 3/2014 | Kumar et al. |
| 2014/0093154 A1 | 4/2014 | Penenberg |
| 2014/0303938 A1 | 10/2014 | Schoenefeld et al. |
| 2014/0378828 A1 | 12/2014 | Penenberg et al. |
| 2015/0088145 A1 | 3/2015 | McCarthy |
| 2015/0088146 A1 | 3/2015 | McCarthy |
| 2015/0117608 A1 | 4/2015 | Lytle et al. |
| 2015/0150523 A1 | 6/2015 | Sirpad et al. |
| 2015/0227679 A1 | 8/2015 | Kamer et al. |
| 2015/0238271 A1 | 8/2015 | Wollowick et al. |
| 2015/0257846 A1 | 9/2015 | Kubiak et al. |
| 2015/0272695 A1 | 10/2015 | Kubiak et al. |
| 2016/0100909 A1 | 4/2016 | Wollowick et al. |
| 2016/0128654 A1 | 5/2016 | Wollowick et al. |
| 2016/0225192 A1 | 8/2016 | Jones et al. |
| 2016/0277650 A1 | 9/2016 | Nagaraja et al. |
| 2017/0042619 A1 | 2/2017 | Brooks |
| 2017/0054663 A1 | 2/2017 | Geiger et al. |
| 2017/0128135 A1 | 5/2017 | McCarthy et al. |
| 2017/0143433 A1 | 5/2017 | Fanson et al. |
| 2017/0165008 A1 | 6/2017 | Finley |
| 2017/0202682 A1 | 7/2017 | McCarthy |
| 2017/0224418 A1 | 8/2017 | Boettner et al. |
| 2017/0258526 A1 | 9/2017 | Lang |
| 2018/0199995 A1 | 7/2018 | Odermatt et al. |
| 2019/0090962 A1 | 3/2019 | Boettner |
| 2019/0350728 A1 | 11/2019 | van der Walt et al. |
| 2020/0085510 A1 | 3/2020 | Wollowick et al. |
| 2020/0100751 A1 | 4/2020 | Wollowick et al. |
| 2020/0323648 A1 | 10/2020 | Samuelson et al. |
| 2020/0352529 A1 | 11/2020 | Wollowick et al. |
| 2021/0196390 A1 | 7/2021 | Wollowick et al. |
| 2021/0361252 A1 | 11/2021 | Wollowick et al. |
| 2022/0211446 A1 | 7/2022 | Wollowick et al. |
| 2022/0323159 A1 | 10/2022 | Boettner et al. |

(56) References Cited

U.S. PATENT DOCUMENTS

2023/0050141 A1    2/2023    Cooper et al.
2023/0277331 A1    9/2023    Beck et al.

FOREIGN PATENT DOCUMENTS

| | | |
|---|---|---|
| EP | 1406203 A2 | 4/2004 |
| EP | 3511905 A1 | 7/2019 |
| EP | 3689285 A1 | 8/2020 |
| JP | 2004105551 A | 4/2004 |
| JP | 2005130928 A | 5/2005 |
| JP | 2005185767 A | 7/2005 |
| JP | 2007151742 A | 6/2007 |
| JP | 2008515512 A | 5/2008 |
| JP | 2009503634 A | 1/2009 |
| JP | 2009136384 A | 6/2009 |
| JP | 2010088892 A | 4/2010 |
| JP | 2011512908 A | 4/2011 |
| JP | 2012020133 A | 2/2012 |
| WO | 2007009263 A1 | 1/2007 |
| WO | 2009108683 A1 | 9/2009 |
| WO | 2011134083 A1 | 11/2011 |
| WO | 2013049534 A1 | 4/2013 |
| WO | 2013175471 A1 | 11/2013 |
| WO | 2014008613 A1 | 1/2014 |
| WO | 2014025305 A1 | 2/2014 |
| WO | 2014127354 A1 | 8/2014 |
| WO | 2015130848 A1 | 9/2015 |

OTHER PUBLICATIONS

Baumgaertner et al., "The Value of the Tip-Apex Distance in Predicting Failure of Fixation of Peritrochanteric Fractures of the Hip," The Journal of Bone and Joint Surgery, Jul. 1995, pp. 1058-1064, vol. 77-A, The Journal of Bone and Joint Surgery, Incorporated.

De Bruijn et al., "Reliability of Predictors for Screw Cutout in Intertrochanteric Hip Fractures," The Journal of Bone and Joint Surgery, Jul. 18, 2012, pp. 1266-1272, vol. 94-A(14), The Journal of Bone and Joint Surgery, Incorporated.

Depuy Orthopaedics, Inc., Corail Total Hip System: Surgical Technique, 2005, pp. 1-16, USA.

European Patent Office, Communication for European Application No. 15755633.3, Sep. 18, 2017, pp. 1-9.

European Patent Office, Communication for European Application No. 16876926.3, Oct. 23, 2019, pp. 1-8.

European Patent Office, Communication for European Application No. 17739110.9, Jul. 6, 2021, pp. 1-6.

European Patent Office, Communication for European Application No. 21170146.1, Jul. 29, 2021, pp. 1-12.

European Patent Office, Summons to attend oral proceedings for European Patent No. 3113710, Feb. 9, 2021, pp. 1-10.

European Patent Office, Summons to attend oral proceedings for European Patent No. 3113710, May 8, 2020, pp. 1-15.

European Patent Office, Supplementary European Search Report for European Application No. 17739110, filed Jun. 25, 2019, pp. 1-2.

Hofmann et al., "Minimizing Leg-Length Inequality in Total Hip Arthroplasty: Use of Preoperative Templating and an Intraoperative X-Ray," The American Journal of Orthopedics, Jan. 2008, pp. 18-23, vol. 37(1).

IP Australia, Examination Report No. 1 for Australian Patent Application No. 2016371212, Mar. 31, 2021, pp. 1-4.

IP Australia, Examination Report No. 1 for Australian Patent Application No. 2017207496, Aug. 23, 2021, pp. 1-3.

Israel Patent Office, International Search Report and Written Opinion for International Application No. PCT/US2015/0017603, Jun. 10, 2015, pp. 1-6.

Japanese Patent Office, Office Action for Japanese Application No. 2016-570943, Jan. 8, 2019, pp. 1-6 (with English translation, pp. 1-7).

Japanese Patent Office, Office Action for Japanese Application No. 2019-186976, Dec. 1, 2020, pp. 1-4 (with English translation, pp. 1-6).

Jaramaz et al., "CupAlign: Computer-Assisted Postoperative Radiographic Measurement of Acetabular Components Following Total Hip Arthroplasty," Medical Image Computing and Computer Assisted Intervention (MICCAI), 1999, pp. 876-882, Springer-Verlag.

Labronici et al., "Positioning of the acetabular component in cemented prostheses—radiograph calculation," Revista Brasileira de Ortopedia (English Edition), 2013, pp. 62-68, vol. 48(1), Elsevier Editora Ltda.

Larose et al., "Post-Operative Measurement of Acetabular Cup Position Using X-ray/CT Registration," Medical Image Computing and Computer-Assisted Intervention (MICCAI), 2000, pp. 1104-1113, Springer-Verlag.

Le Duff et al., "Benefits of Thin-Shelled Acetabular Components for Metal-on-Metal Hip Resurfacing Arthroplasty," Journal of Orthopaedic Research, Jun. 1, 2010, pp. 1665-1670, vol. 28, Wiley Periodicals, Inc.

Liaw et al., "A New Tool for Measuring Cup Orientation in Total Hip Arthroplasties from Plain Radiographs," Clinical Orthopaedics and Related Research, Oct. 2006, pp. 134-139, vol. 451, Lippincott Wiliams & Wilkins.

Lu et al., "Reliability and Validity of Measuring Acetabular Component Orientation by Plain Anteroposterior Radiographs," Clinical Orthopaedics and Related Research, May 4, 2013, pp. 2987-2994, vol. 471, Springer.

Mann et al., "Radiographic Evaluation of the Wrist: What Does the Hand Surgeon Want to Know?" Radiology, Jul. 1992, pp. 15-24, vol. 184.

Matta et al., "Single-Incision Anterior Approach for Total Hip Arthroplasty on an Orthopaedic Table," Clinical Orthopaedics and Related Research, Dec. 2005, pp. 115-124, vol. 441, Lippincott Williams & Wilkins.

Nam et al., "Leg-length Inequalities Following THA Based on Surgical Technique", Orthopedics, Apr. 2013, pp. e395-e400, vol. 36(4).

Penney et al., "Postoperative Calculation of Acetabular Cop Position Using 2-D-3-D Registration," IEEE Transactions on Biomedical Engineering, Jul. 2007, pp. 1342-1348, vol. 54(7), IEEE.

Russian Federal Institute of Intellectual Property, International Search Report for International Application No. PCT/US2016/067587, May 25, 2017, pp. 1-2.

Russian Federal Institute of Intellectual Property, Written Opinion for International Application No. PCT/US2016/067587, May 25, 2017, pp. 1-5.

Alvarez et al., "Fluoroscopic Imaging of Acetabular Cup Position During THA Through a Direct Anterior Approach," Orthopedics, Oct. 2013, pp. 776-777, vol. 36, No. 10.

Alvarez, "Fluoroscopic Imaging of Acetabular Cup Position During THA Through a Direct Anterior Approach," Orthopedics, Jan. 2014, p. 12, vol. 37, No. 1.

Babisch et al., "The Rationale for Tilt-Adjusted Acetabular Cup Navigation," The Journal of Bone & Joint Surgery, Feb. 2008, pp. 357-365, vol. 90-A, No. 2.

Blondel et al., "Sacro-femoral-pubic angle: a coronal parameter to estimate pelvic tilt," European Spine Journal, 2012, pp. 719-724, vol. 21, Springer-Verlag.

Brown et al., "Impingement in total hip replacement: mechanisms and consequences," Current Orthopaedics, 2008, pp. 376-391, vol. 22, Elsevier, Inc.

Lewinnek et al., "Dislocation after Total Hip-Replacement Arthroplasties," The Journal of Bone and Joint Surgery, Mar. 1978, pp. 217-220, vol. 60-A(2), The Journal of Bone and Joint Surgery, Inc.

Maratt et al., "Pelvic Tilt in Patients Undergoing Total Hip Arthroplasty: When Does it Matter?" The Journal of Arthroplasty, Mar. 2015, pp. 387-391, vol. 30(3), Elsevier Inc.

Miki et al., "Risk of edge loading and prosthesis impingement due to posterior pelvic tilting after total hip arthroplasty," Clinical Biomechanics, 2014, pp. 607-613, vol. 29, No. 4, Elsevier, Inc.

(56) References Cited

OTHER PUBLICATIONS

Murray, "The Definition and Measurement of Acetabular Orientation," The Journal of Bone and Joint Surgery, Mar. 1993, pp. 228-232, vol. 75-B(2), British Editorial Society of Bone and Joint Surgery.

Zhu et al., "Quantification of Pelvic Tilt in Total Hip Arthroplasty," Clinical Orthopaedics and Related Research, Aug. 28, 2009, pp. 571-575, vol. 468(2), Springer.

* cited by examiner

SYSTEMS AND METHODS FOR INTRA-OPERATIVE IMAGE ANALYSIS

CROSS-REFERENCE TO RELATED APPLICATIONS

This application is a continuation of U.S. patent application Ser. No. 16/938,912, filed Jul. 24, 2020, which is a continuation of U.S. patent application Ser. No. 14/995,057, filed Jan. 13, 2016, now U.S. Pat. No. 10,765,384, which is a continuation-in-part of U.S. patent application Ser. No. 14/630,300, filed Feb. 24, 2015, now U.S. Pat. No. 10,758,198, which claim the benefit of U.S. Provisional Application No. 61/944,520, filed Feb. 25, 2014, U.S. Provisional Application No. 61/948,534, filed Mar. 5, 2014, U.S. Provisional Application No. 61/980,659, filed Apr. 17, 2014, U.S. Provisional Application No. 62/016,483, filed Jun. 24, 2014, U.S. Provisional Application No. 62/051,238, filed Sep. 16, 2014, U.S. Provisional Application No. 62/080,953, filed Nov. 17, 2014, and U.S. Provisional Application No. 62/105,183, filed Jan. 19, 2015. The present application is also related to U.S. patent application Ser. No. 14/974,225, filed Dec. 18, 2015, by the present inventors, which issued as U.S. Pat. No. 10,433,914 on Oct. 8, 2019. The entire contents of each of the above applications are incorporated herein by reference.

TECHNICAL FIELD

The invention relates to analysis of images of features within a patient and more particularly to accurately analyzing such images during surgery.

BACKGROUND

Orthopaedic surgeons have the option of utilizing computer-assisted navigation systems to provide intraoperative surgical guidance. For example, computer navigation can provide data on functional parameters such as leg length and offset changes during hip arthroplasty. The purported benefits of computer navigation include reduction of outliers and adverse outcomes related to intraoperative positioning of surgical hardware.

Despite obvious clinical benefit, these systems have had limited adoption due to their expense, the learning curve and training requirements for surgeons and, for some systems, the additional procedure and time associated with hardware insertion into the patient. Surgeons that do not use these systems are limited to traditional techniques that are generally based on visual analysis and surgeon experience. However, these techniques are inconsistent, often leading to outliers in functional parameters which may affect patient satisfaction and implant longevity.

Details of one such technique, specifically used in a minimally invasive hip arthroplasty technique referred to as the direct anterior approach, are mentioned in the description of a total hip arthroplasty surgery, by Matta et al. in "Single-incision Anterior Approach for Total hip Arthroplasty on an Orthopaedic Table", Clinical Ortho. And Related Res. 441, pp. 115-124 (2005). The intra-operative technique described by Matta et al. is time-consuming and has a high risk of inaccuracy due to differences in rotation, magnification, and/or scaling of various images, because the technique relies upon acquiring a preoperative and intraoperative image that are scaled and positioned equivalently. The technique also requires consistent patient positioning in the preoperative and intraoperative images, including positioning of the femur relative to the pelvis. Maintaining femoral position while performing hip arthroplasty can pose a significant and often unrealistic challenge to a surgeon that is focused on performing a procedure. The high risk of inaccurate interpretation using this technique has limited its utility in guiding surgical decision making.

What appears to be a software implementation of this technique is described by Penenberg et al. in U.S. Patent Publication No. 2014/0378828, which is a continuation-in-part application of U.S. Pat. No. 8,831,324 by Penenberg. While the use of a computer system may facilitate some aspects of this technique, the underlying challenges to the technique are consistent with the challenges to Matta's approach, and limit the system's potential utility.

The challenge of accounting for differences in femoral positioning, ever-present in existing non-invasive guidance technologies for hip arthroplasty, could be solved by developing a system and method that corrects for deviations between preoperative and intraoperative femoral positioning.

It is therefore desirable to have a non-invasive system and method that provides intraoperative guidance and data by correcting for deviations in femoral positioning between preoperative and intraoperative images.

SUMMARY

An object of the present invention is to quantify restoration of orthopaedic functionality at a surgical site within a patient, even during a surgical procedure.

Another object of the present invention is to provide image analysis and feedback information to enable better fracture reduction and/or optimal implant selection during the surgery.

Yet another object of the present invention is to capture and preserve a digital record of patient results for data collection and quality improvements in surgical procedures.

A still further object of the present invention is to improve the outcome of bone repositioning, fracture repair, and/or fixation within a patient.

This invention results from the realization that postoperative change in offset and leg length can be accurately estimated during surgery by overlaying or otherwise comparing preoperative and intraoperative images that have been consistently scaled based on pelvic anatomy, generating consistent femoral landmarks in each image, and calculating the vector difference between femoral landmarks after correcting for possible differences in femoral positioning between the two images relative to the pelvis.

This invention features a system to analyze images at a surgical site within a patient, the surgical site including at least one skeletal bone such as a pelvis and at least one articulating bone such as a femur that has a longitudinal axis and articulates with the skeletal bone at a joint. In one embodiment, the system includes an image capture module capable of acquiring (i) at least one reference image including one of a preoperative image of the surgical site and a contralateral image on an opposite side of the patient from the surgical site, and (ii) at least an intraoperative image of the site after an implant has been affixed to the articulating bone. A landmark identification module is capable of receiving the reference and intraoperative images and generates at least one reference landmark point on at least one anatomical feature on the articulating bone in the reference image and at least one intraoperative landmark point on that anatomical feature in the intraoperative image. An image comparison module is capable of identifying (i) an estimation of at least the first center of rotation of the implant in at least one of the reference image and the intraoperative image and (ii) the longitudinal axis of the articulating bone in each of the reference image and intraoperative image. An analysis module is capable of utilizing differences between the orientation of the articulating bone in the reference image relative to the orientation of the articulating bone in the intraoperative image to analyze at least one of offset and length differential.

In some embodiments, the first and second images are provided by the image capture module to the landmark identification module in a digitized format. In certain embodiments, the analysis module calculates a difference angle between the longitudinal axis of the femur in the reference image relative to the longitudinal axis of the femur in the intraoperative image and then estimates a corrected landmark point, such as a corrected intraoperative landmark point, based on that difference angle. In one embodiment, the analysis module estimates the corrected intraoperative landmark point by calculating a first radius between the estimated center of rotation and the intraoperative landmark and then selecting the corrected intraoperative landmark point at a second radius spaced at the difference angle from the first radius. In certain embodiments, the analysis module calculates length differential by estimating distance from the reference landmark point to the corrected intraoperative landmark point in a direction parallel to the longitudinal axis of the femur in the reference image, and/or calculates offset by estimating distance from the reference landmark point to the corrected intraoperative landmark in a direction perpendicular to the longitudinal axis of the femur in the reference image.

In certain embodiments, at least one of the image comparison module, the landmark identification module and the image comparison module identifies at least one stationary point on the skeletal bone in each of the reference image and intraoperative image, and at least one of the image comparison module, the landmark identification module and the image comparison module aligns the reference image and intraoperative image according to at least the stationary point in each image. In one embodiment, aligning includes overlaying one of the reference image and intraoperative image on the other of the reference image and intraoperative image.

In some embodiments, the reference image and the intraoperative image are at least one of aligned and scaled relative to each other prior to the analysis module analyzing offset and length differential. In one embodiment, at least two stationary points are generated on the skeletal bone in the reference image to establish a reference stationary base and at least two stationary points are generated on the skeletal bone in the intraoperative image to establish an intraoperative stationary base, and at least one of the image comparison module, the landmark identification module and the image comparison module utilizes the reference and intraoperative stationary bases to accomplish at least one of image alignment and image scaling. In another embodiment, at least one of the image comparison module, the landmark identification module and the image comparison module provides at least relative scaling of one of the reference and intraoperative images to match the scaling of the other of the reference and intraoperative images.

This invention also features a system including a memory, a user interface having a display capable of providing at least visual guidance to a user of the system, and a processor, with the processor executing a program performing the steps of acquiring (i) at least one digitized reference image including one of a preoperative image of a surgical site with skeletal and articulating bones and a contralateral image on an opposite side of the patient from the surgical site, and (ii) at least one digitized intraoperative image of the site after an implant has been affixed to the articulating bone. The processor receives the reference and intraoperative images and generates at least one reference landmark point on at least one anatomical feature on the articulating bone in the reference image and at least one intraoperative landmark point on that anatomical feature in the intraoperative image. The processor identifies (i) an estimation of at least the first center of rotation of the implant in at least one of the reference image and the intraoperative image and (ii) the longitudinal axis of the articulating bone in each of the reference image and intraoperative image. One or more differences between the orientation of the articulating bone in the reference image relative to the orientation of the articulating bone in the intraoperative image are utilized to analyze at least one of offset and length differential.

This invention further features a method including acquiring (i) at least one reference image including one of a preoperative image of a surgical site with skeletal and articulating bones and a contralateral image on an opposite side of the patient from the surgical site, and (ii) at least one intraoperative image of the site after an implant has been affixed to the articulating bone. The method further includes receiving the reference and intraoperative images and generating at least one reference landmark point on at least one anatomical feature on the articulating bone in the reference image and at least one intraoperative landmark point on that anatomical feature in the intraoperative image. The method includes identifying (i) an estimation of at least the first center of rotation of the implant in at least one of the reference image and the intraoperative image and (ii) the longitudinal axis of the articulating bone in each of the reference image and intraoperative image. One or more differences between the orientation of the articulating bone in the reference image relative to the orientation of the articulating bone in the intraoperative image are utilized to analyze at least one of offset and length differential.

In some embodiments, aligning includes overlaying one of the reference image and intraoperative image on the other of the reference image and intraoperative image. In certain embodiments, the pelvis of the patient is selected as the skeletal bone and a femur is selected as the articulating bone, and the skeletal component of the implant is an acetabular cup and the articulating bone component includes a femoral stem having a shoulder and pivotally connectable to the acetabular cup to establish the first center of rotation for the implant. The landmark point on the articulating bone is identified to have a known location relative to the greater trochanter on the femur of the patient.

BRIEF DESCRIPTION OF THE DRAWINGS

In what follows, preferred embodiments of the invention are explained in more detail with reference to the drawings, in which.

DETAILED DESCRIPTION OF THE DRAWINGS

Figure 1:
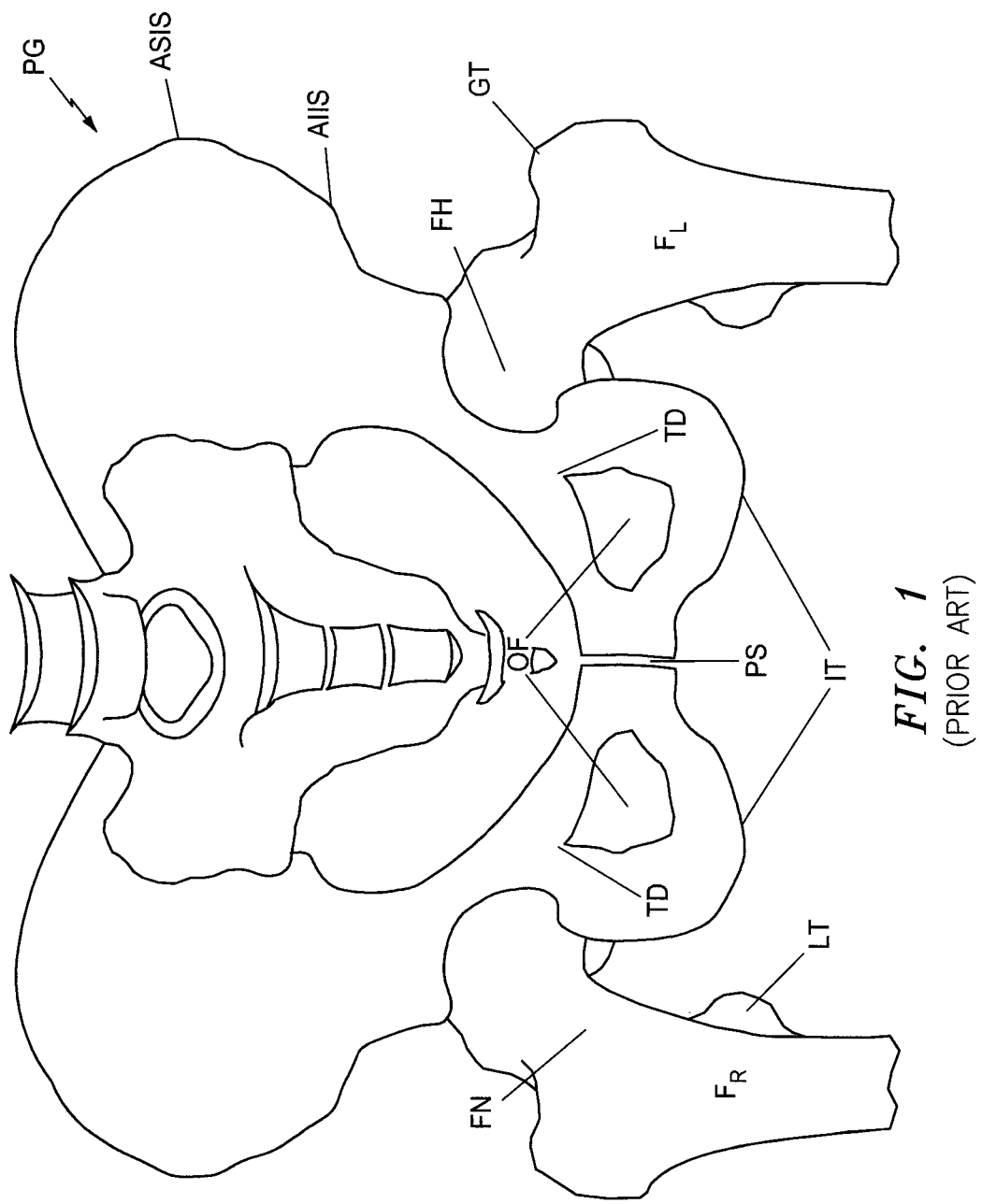
FIG. 1 is a schematic image of a frontal, X-ray-type view of a pelvic girdle of a patient illustrating various known anatomical features.

This invention may be accomplished by a system and/or method that acquire (i) at least one reference image including one of a preoperative image of a surgical site with skeletal and articulating bones and a contralateral image on an opposite side of the patient from the surgical site, and (ii) at least one intraoperative image of the site after an implant has been affixed to the articulating bone. The reference and intraoperative images are received and at least one reference landmark point is generated on at least one anatomical feature on the articulating bone, such as on the greater trochanter of a femur, in the reference image and at least one intraoperative landmark point on that anatomical feature in the intraoperative image. At least the first center of rotation of the implant is estimated in at least one of the reference image and the intraoperative image, and the longitudinal axis of the articulating bone is identified in each of the reference image and intraoperative image. One or more differences between the orientation of the articulating bone in the reference image relative to the orientation of the articulating bone in the intraoperative image are utilized to analyze at least one of offset and length differential.

Broadly, some techniques according to the present invention, referred to by the present inventors as "Image Overlay", place one image over another image during analysis to generate a combined overlapped image. Previous approaches for the 'Image Overlay' technique made use of a pelvic reference line having two or more points to scale and align a preoperative image and an intraoperative image. The pelvic reference line having two or more points is also referred to as a "stationary base" as defined in U.S. patent application Ser. No. 14/630,300, filed Feb. 24, 2015, sometimes referred to herein as "parent application," now U.S. Pat. No. 10,758,198.

Alternative approaches for "Image Overlay" technique according to the present invention obviate the need for the pelvic reference line or other stationary base. In some constructions, these alternatives instead rely upon certain image acquisition techniques, certain image manipulation techniques, certain known imaging information, and/or direct user manipulation to create consistent scale and alignment between (i) at least one of a preoperative image and an inverted contralateral image and (ii) an intraoperative image.

Additionally, any change in positioning of the femur in the two images, relative to the pelvis, would adversely affect calculations in previous approaches of this technique. Maintaining femoral position while performing hip arthroplasty can pose a significant and often unrealistic challenge to a surgeon that is focused on performing a surgical procedure. Various approaches for the 'Image Overlay' technique according to the present invention can correct for deviations in femoral positioning between preoperative and intraoperative images by mathematically correcting for any deviation in femoral position in at least one of the visual output and calculation output of offset and leg length. Presently preferred techniques, both with and without image overlay, are described in more detail below in relation to FIGS. 17-23.

In general, accurate analysis of two images of a patient is directly related not only to how similar the two images are, but also how similarly the images are aligned with respect to scale and alignment, including rotation and translation.

Using conventional techniques, a user would have to manually adjust the images and/or retake multiple images to achieve this goal, something that would be difficult to do reliably and accurately. Utilizing two or more points as a stationary base according to the present invention in each image enables accurate analysis of the two images. Furthermore, the present Image Overlay technique can analyze how "similar" these images are to give the user feedback as to how accurate the results are, that is, to provide a confidence interval. To obtain useful information, the images (the "intraop" intra-operative image and a "preop" pre-operative image, for example) preferably are scaled similarly and rotated similarly, at least relative to each other.

For some constructions of image analysis according to the present invention, preferably at least one stationary base and at least one anatomical landmark are selected, at least for scaling and alignment of the images. The term "stationary base", also referred to herein as a "stable base", means a collection of two or more points, which may be depicted as a line or other geometric shape, drawn on each of two or more images that includes at least one anatomical feature that is present in the two or more images of a region of a patient. For example, different images of a pelvic girdle PG of a patient, FIG. 1, typically show one or both obturator foramen OF and a central pubic symphysis PS, which the present inventors have recognized as suitable reference points or features for use as part of a stationary base according to the present invention. Other useful anatomical features, especially to serve as landmarks utilized according to the present invention, include femoral neck FN and lesser trochanter LT, shown on right femur $F_R$, and femoral head FH and greater trochanter GT shown on left femur $F_L$, for example. Femoral head FH engages the left acetabulum of the pelvic girdle PG. Also shown in FIG. 1 are ischial tuberosities IT at the bottom of the ischium, a "tear drop" TD relating to a bony ridge along the floor of the acetabular fossa, and the anterior superior iliac spine ASIS and the anterior inferior iliac spine AIIS of the ileum.

In general, a longer stationary base is preferred over a shorter stationary base, because the longer base, especially if it is a line, will contain more pixels in images thereof and will increase accuracy of overlays and scaling according to the present invention. However, the further the stationary base is from the area of anatomical interest, the greater the risk of parallax-induced error. For example, if the area of interest is the hip joint, then the ideal stationary base will be near the hip. In some procedures involving hip surgery, for example, a stationary base line begins at the pubic symphysis PS, touches or intersects at least a portion of an obturator foramen OF, and extends to (i) the "tear drop" TD, or (ii) the anterior interior iliac spine AIIS. Of course, only two points are needed to define a line, so only two reliable anatomical features, or two locations on a single anatomical feature, are needed to establish a stationary base utilized according to the present invention. More complex, non-linear stationary bases may utilize additional identifiable points to establish such non-linear bases.

Additionally, at least one identifiable anatomic "landmark", "stationary point" or "error point", or a set of landmarks stationary points or error points, is selected to be separate from the stationary base; the one or more landmarks, stationary points or error points are utilized in certain constructions to analyze the accuracy of the overlay process. This additional anatomic feature preferably is part of the stationary anatomy being anatomically compared. For example, the inferior portion of the ischial tuberosity IT can be identified as an additional stationary point or error point. This anatomic feature, in conjunction with the stationary base, will depict any differences or errors in pelvic anatomy or the overlay which will enable the physician to validate, or to have more confidence in, the output of the present system. As generally utilized herein: (i) a "stationary point" refers to a point on a relatively stationary bone such as on the pelvis; (ii) a "landmark point" is located on an articulating bone such as a femur; (iii) an "error point" is preferably on pelvis and spaced from other points; and (iv) a "fixed point" is located on an implant, such as the shoulder of a femoral stem prosthesis.

The term "trial hip prosthetic" is utilized herein to designate an initial implant selected by a surgeon as a first medical device to insert at the surgical site, which is either the right side or the left side of a patient's hip in certain constructions. In some techniques, the trial prosthetic is selected based on initial digital templating similar to the procedure described the parent application.

The term "digital representation" or "digital annotation" as utilized herein includes a digital line having at least two points, e.g. a line representing a longitudinal axis or a diameter of an implant or a bone, or a digital circle or other geometric shape which can be aligned with an implant or a bone intraoperatively and then placed in a corresponding location in a preoperative image, or visa versa.

Figure 2:
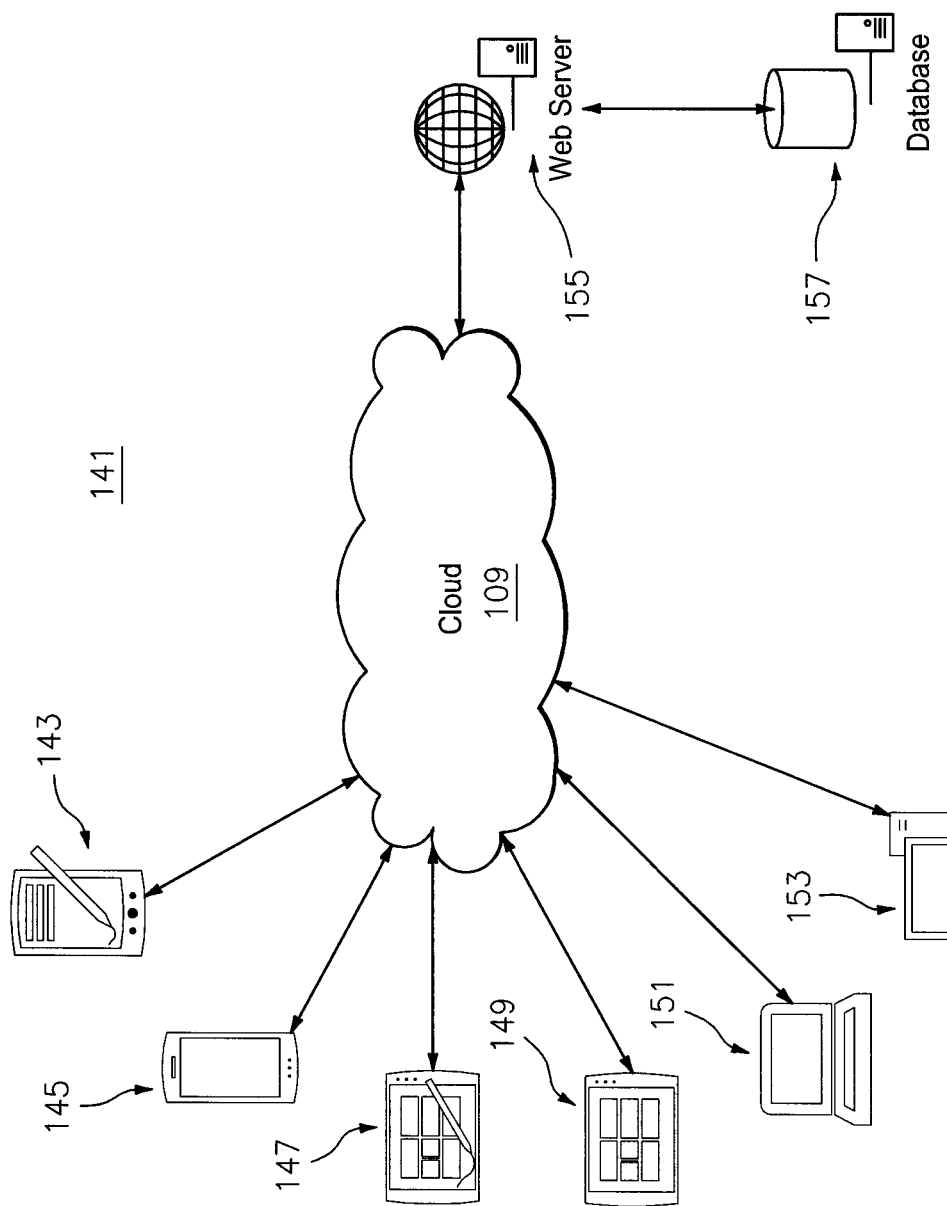
FIG. 2 is a schematic diagram illustrating how multiple types of user interfaces can be networked via a cloud-based system with data and/or software located on a remote server.

FIGS. 2-16 herein correspond to FIGS. 4B, 7-16, 52-54 and 70, respectively, in the parent application. FIG. 2 herein is a schematic diagram of system 141 according to the present invention illustrating how multiple types of user interfaces in mobile computing devices 143, 145, 147 and 149, as well as laptop 151 and personal computer 153, can be networked via a cloud 109 with a remote server 155 connected through web services. Data and/or software typically are located on the server 155 and/or storage media 157.

Software to accomplish the techniques described herein is located on a single computing device in some constructions and, in other constructions such as system 141, FIG. 2, is distributed among a server 155 and one or more user interface devices which are preferably portable or mobile. In some techniques a digitized X-ray image of the hip region of a patient along a frontal or anterior-to-posterior viewing angle is utilized for a screen view on a display and, in other techniques, a digital photograph "secondary" image of a "primary" X-ray image of the hip region of a patient along a frontal or anterior-to-posterior viewing angle is utilized for the screen view. In one construction, the screen view is shown on a computer monitor and, in another construction, is shown on the screen or viewing region of a tablet or other mobile computing device.

Figures 3, 4:
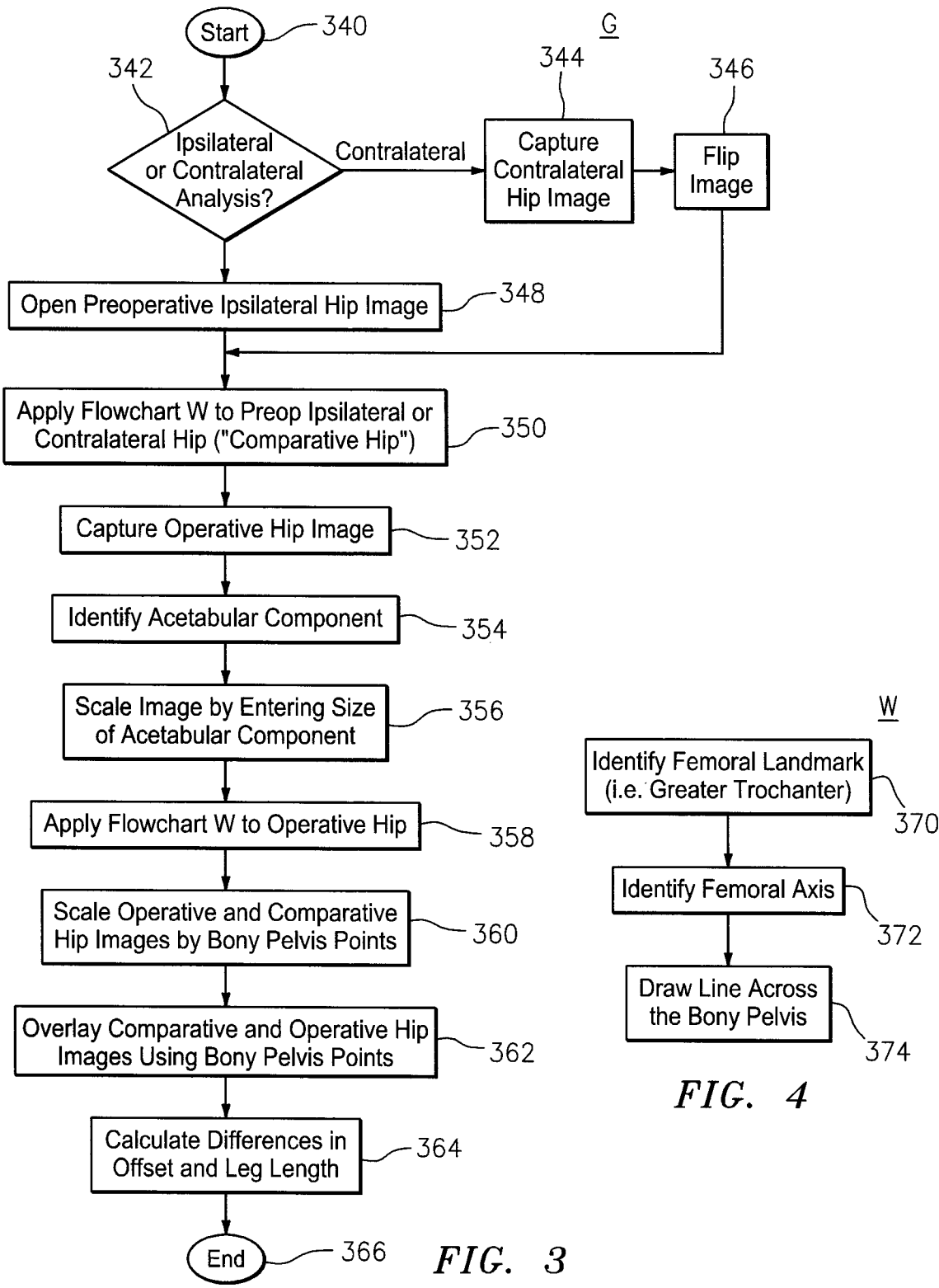
FIG. 3 is a Flowchart G showing technique flow for both contralateral and ipsilateral analysis.
FIG. 4 is a Flowchart W of several functions performed for hip analysis.

Flowchart G, FIG. 3, shows technique flow for both contralateral and ipsilateral analysis. This technique is commenced, step 340, and either contralateral or ipsilateral analysis is selected, step 342. For contralateral analysis, the contralateral hip image is captured, step 344, and the image is flipped, step 346. For ipsilateral analysis, the preoperative ipsilateral hip image is opened, step 348. For both types of analysis, Flowchart W is applied, step 350.

Figure 5:
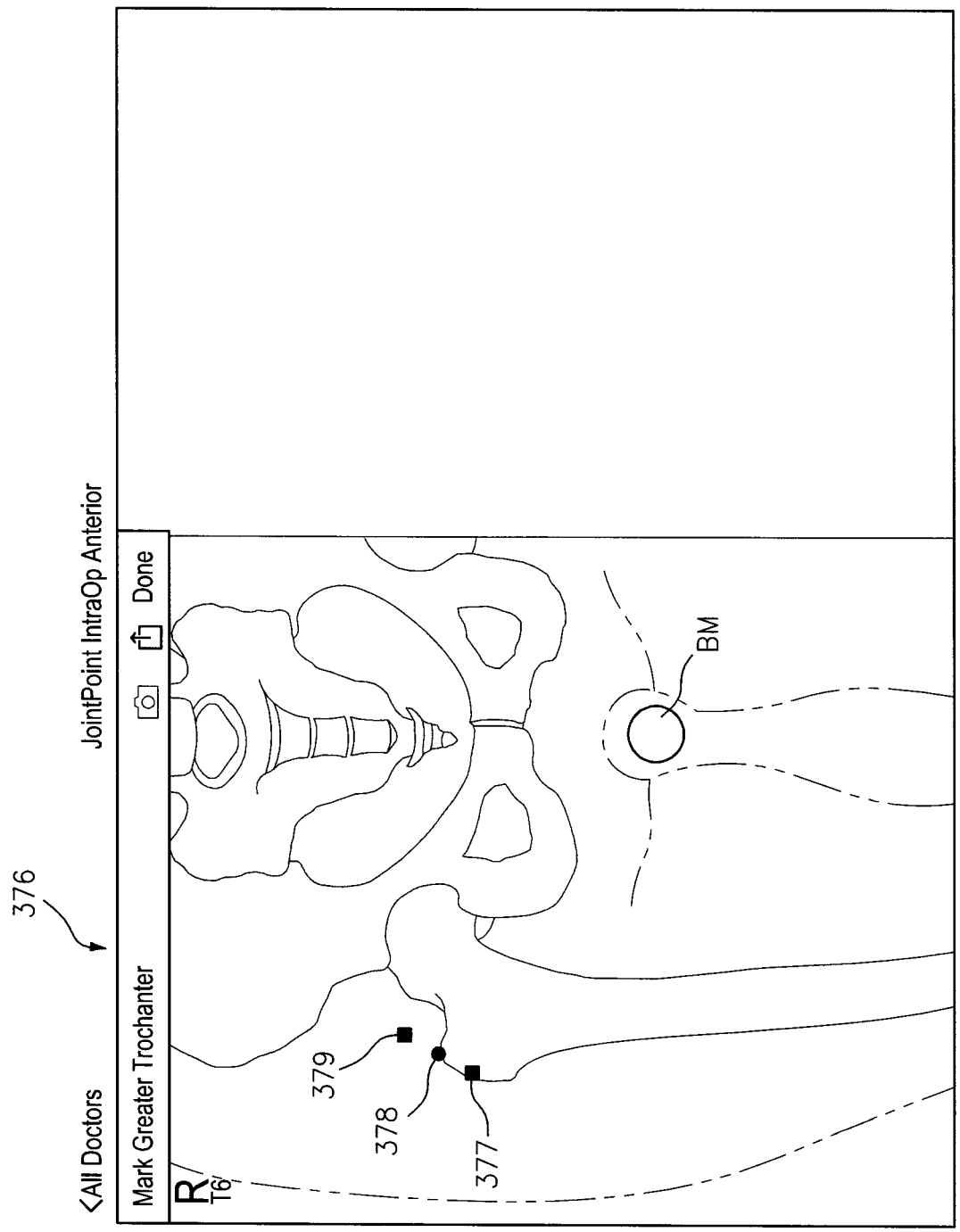
FIG. 5 is an image of the right side of a patient's hip prior to an operation and showing a marker placed on the greater trochanter as a landmark or reference point.
Figure 6:
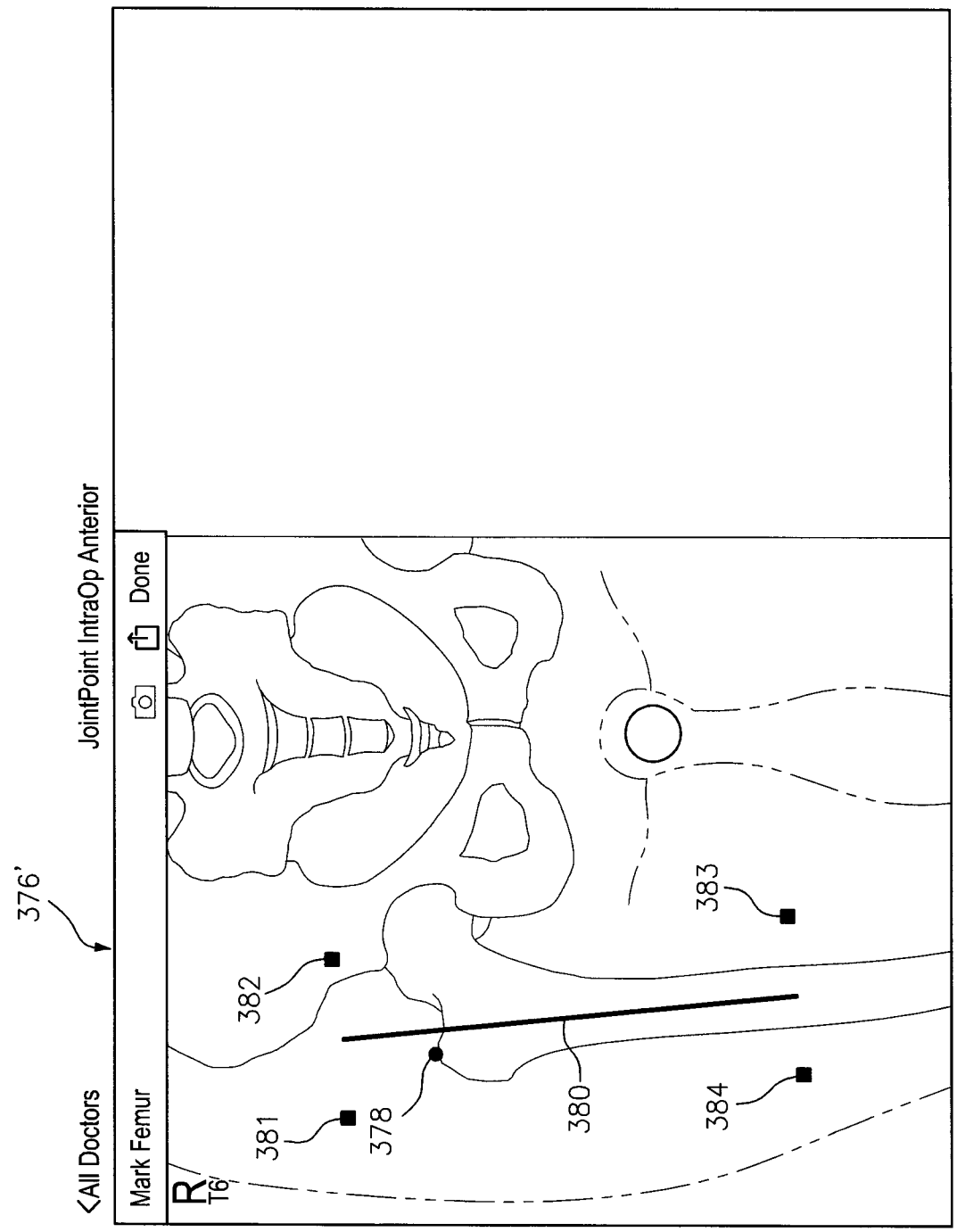
FIG. 6 is an image similar to FIG. 5 showing a reference line, drawn on (i) the pre-operative, ipsilateral femur or (ii) the contra-lateral femur, to represent the longitudinal axis of the femur.
Figure 7:
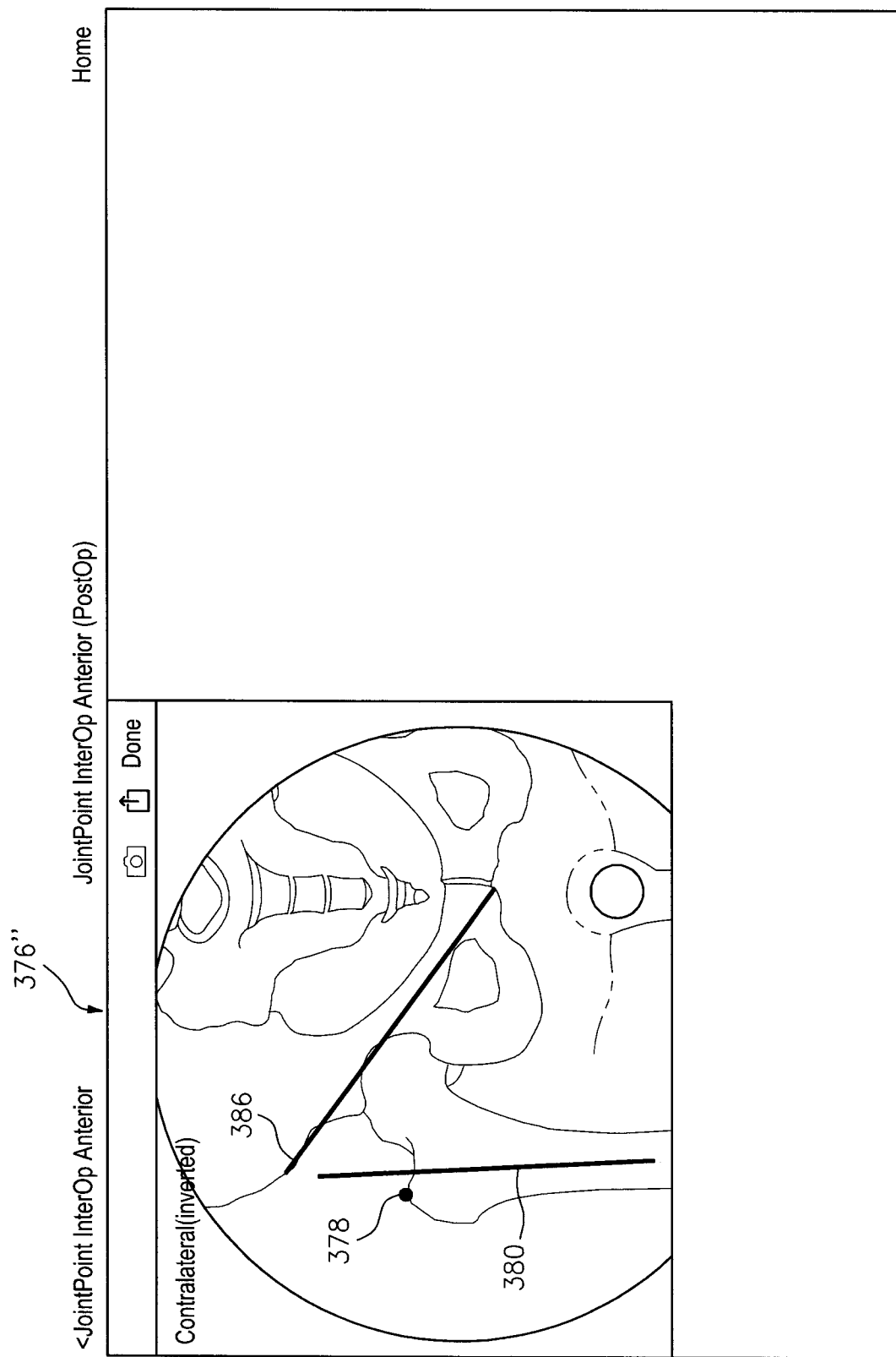
FIG. 7 is an image similar to FIG. 6 with a line drawn across the pelvic bone intersecting selected anatomical features.
Figure 8:
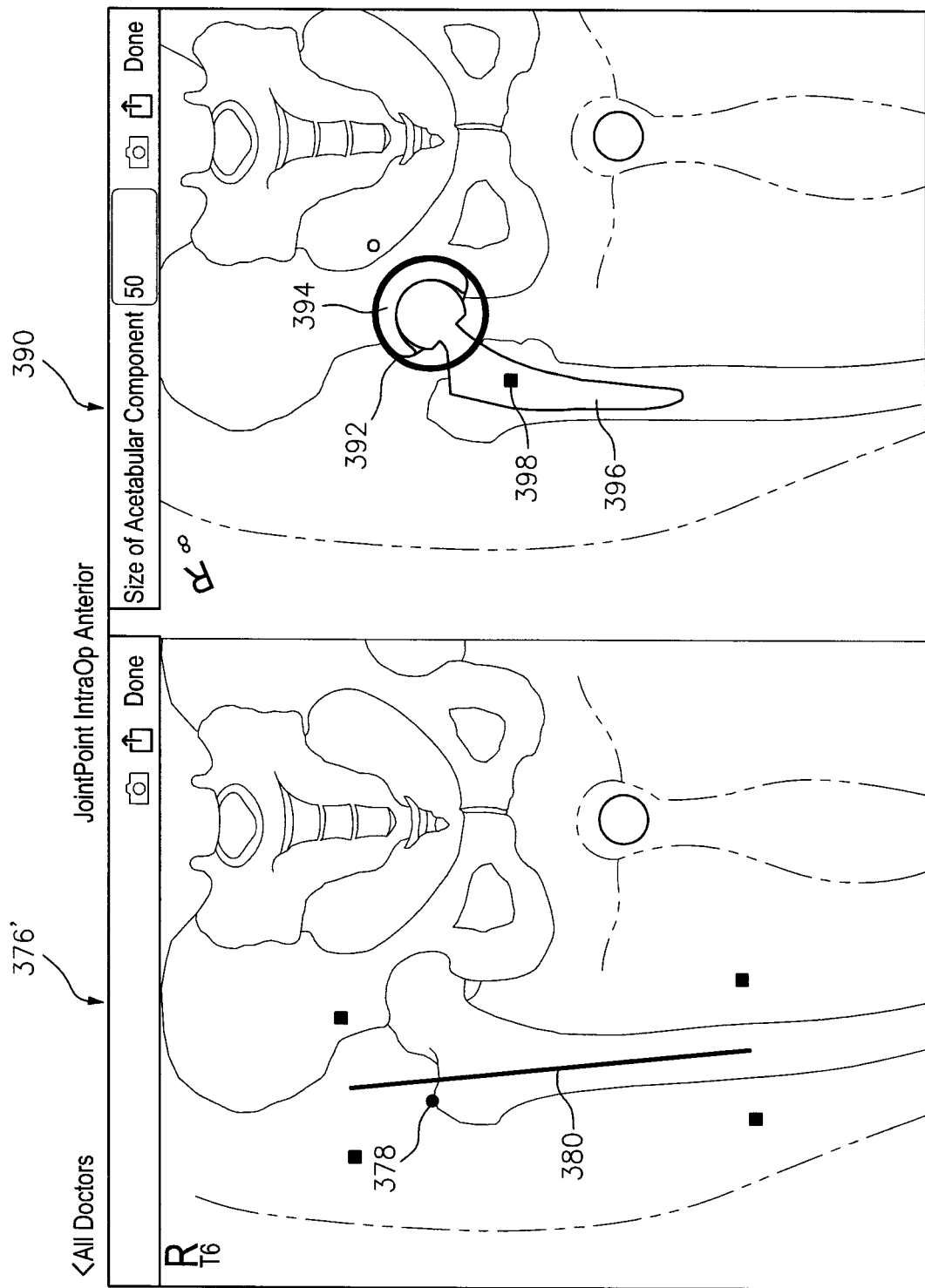
FIG. 8 is a schematic screen view of two images, the left-hand image representing a pre-operative view similar to FIG. 6 and the right-hand image representing an intra-operative view with a circle placed around the acetabular component of an implant to enable rescaling of that image.
Figure 10:
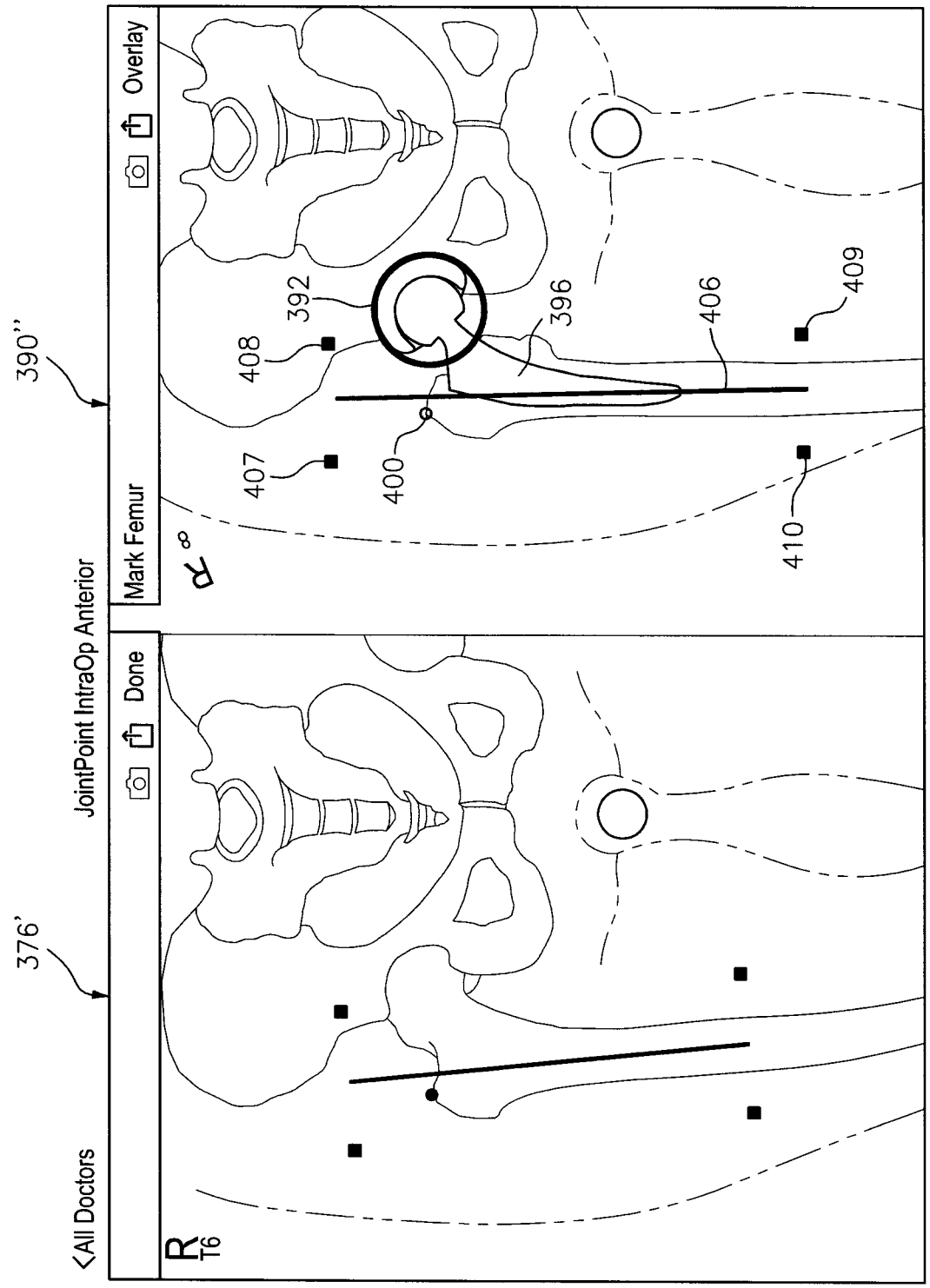
FIG. 10 is a schematic screen view similar to FIG. 9 with a reference line drawn on the intra-operative femur in the right-hand view.
Figure 11:
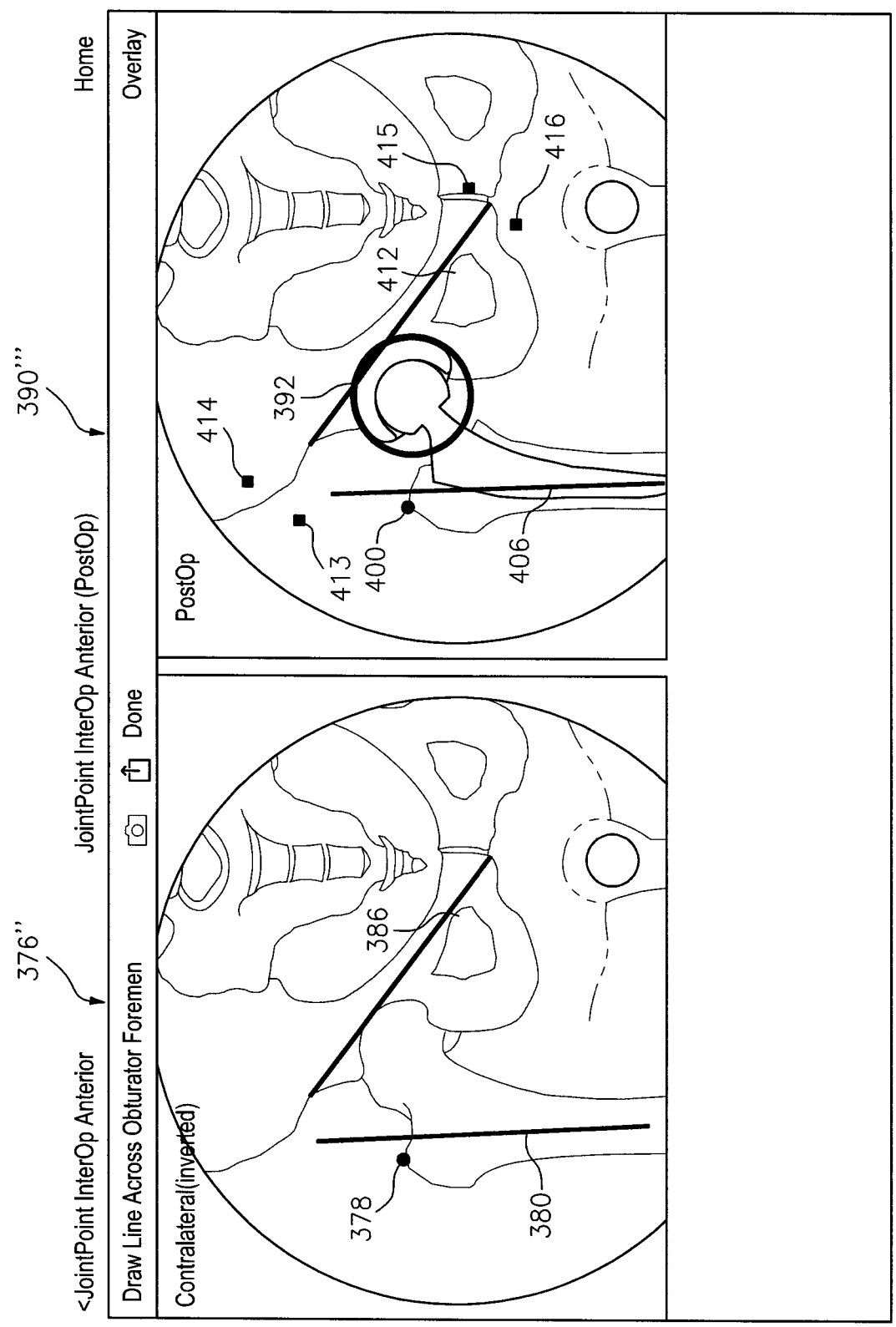
FIG. 11 is an image similar to FIGS. 7 and 10 with a line drawn across the obturator foramen in both pre- and intra-operative views.

Flowchart W, FIG. 4, after being activated by step 350, FIG. 3, guides a user to identify a femoral landmark such as the greater trochanter in step 370, FIG. 4, and then the femoral axis is identified, step 372, which corresponds to the longitudinal axis of the femur in that image. These steps are illustrated in FIGS. 5 and 6, below. A line is then drawn across the bony pelvis, step 374, as shown in FIG. 7. The technique proceeds to capturing an operative hip image, step 352, FIG. 3, and identifying an acetabular component, step 354, such as shown in FIG. 8 below. Acetabular components are also shown in and discussed relative to FIGS. 9 and 10 below. The image is scaled by entering the size of the acetabular component, step 356, and Flowchart W, FIG. 4, is then applied to the operative hip, step 358. The operative and comparative hip images are scaled by a stationary base generated by selecting at least two reference points on the bony pelvis, step 360, such as shown in FIG. 11. The scaled images are then overlaid in step 362 using the bony pelvis points, such as the overlaid lines 386 and 412 shown in FIG. 12. Differences in offset and leg length are calculated, step 364, and the technique is terminated, step 366.

One currently preferred implementation of the JointPoint IntraOp™ Anterior system, which provides the basis for intraoperative analysis of the anterior approach to hip surgery, is illustrated in relation to FIGS. 9-22 in the parent application; FIGS. 9-16 are described herein as FIGS. 5-12. FIG. 5 herein is an image 376 of the right side of a patient's hip prior to an operation and showing a marker 378, bracketed by reference squares 377 and 379, placed by a user as guided by the system, or placed automatically via image recognition, on the greater trochanter as a landmark or reference point. FIG. 6 is an image 376' similar to FIG. 5 showing a reference line 380, bracketed by reference squares 381, 382, 383 and 384, drawn on (i) the pre-operative, ipsilateral femur or (ii) the contra-lateral femur, to represent the longitudinal axis of the femur. FIG. 7 is an image 376" similar to FIG. 6 with a line 386, defined by two end-points, which is drawn across the pelvic bone intersecting selected anatomical features.

Figure 9:
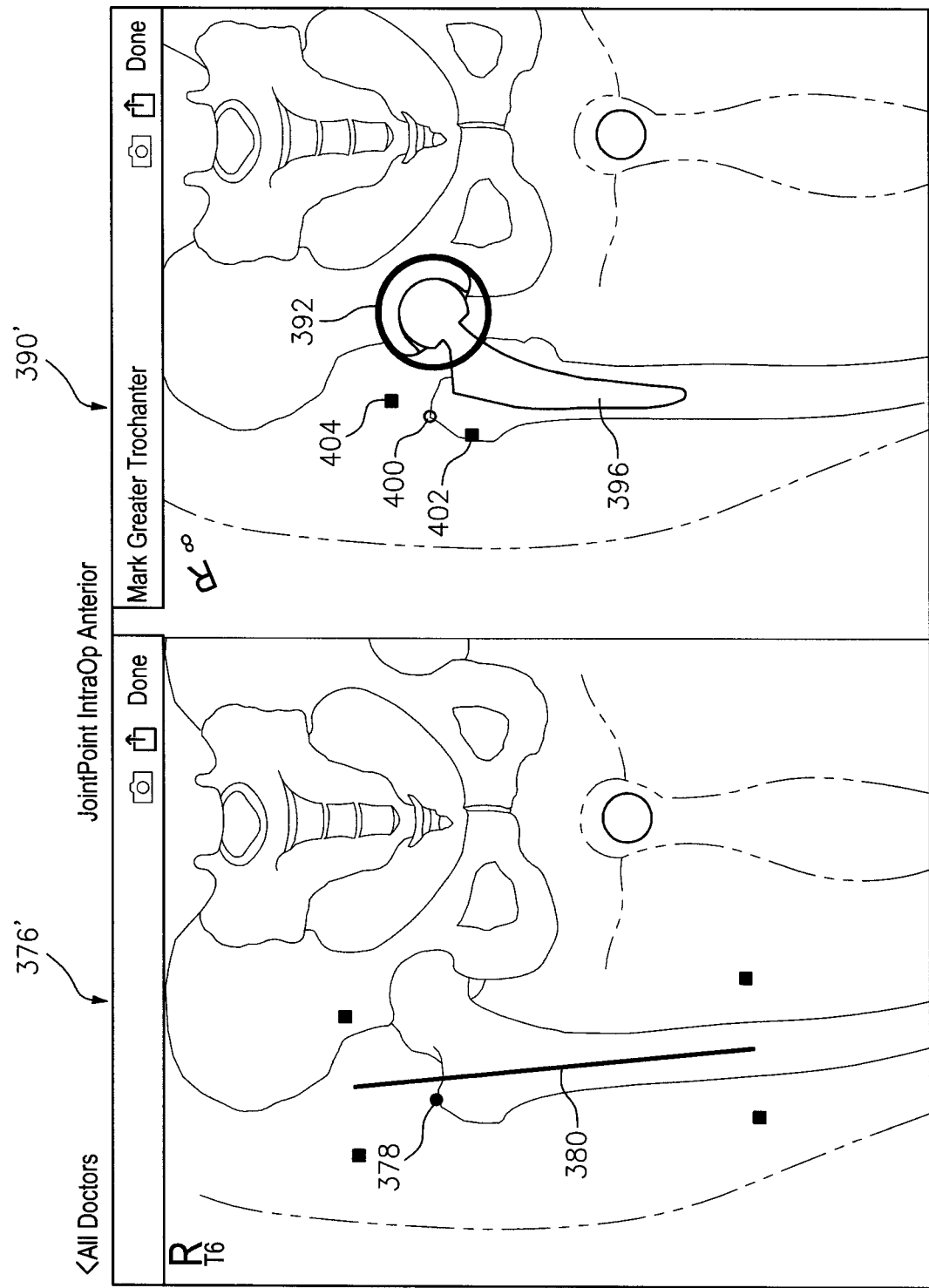
FIG. 9 is a schematic screen view similar to FIG. 8 indicating marking of the greater trochanter of the right-hand, intra-operative image as a femoral landmark.

FIG. 8 is a schematic screen view of two images, the left-hand image 376' representing a pre-operative view similar to FIG. 6 and the right-hand image 390 representing an intra-operative view with a circle 392 placed around the acetabular component 394 of an implant 398 to enable rescaling of that image. In some constructions, circle 392 is placed by an image recognition program and then manually adjusted by a user as desired. Reference square 398 designates implant 398 to the user. FIG. 9 is a schematic screen view similar to FIG. 8 indicating marking of the greater trochanter of the right-hand, intra-operative image 390' as a femoral landmark 400, guided by reference squares 402 and 404. FIG. 10 is a schematic screen view similar to FIG. 9 with a reference line 406 drawn on the intra-operative femur in the right-hand view 390", guided by reference squares 407, 408, 409 and 410.

FIG. 11 is an image similar to FIGS. 7 and 10 with a line 386, 412 drawn across the obturator foremen in both pre- and intra-operative views 376" and 390''', respectively. Reference squares 413, 414, 415 and 416 guide the user while drawing reference line 412.

Figure 12:
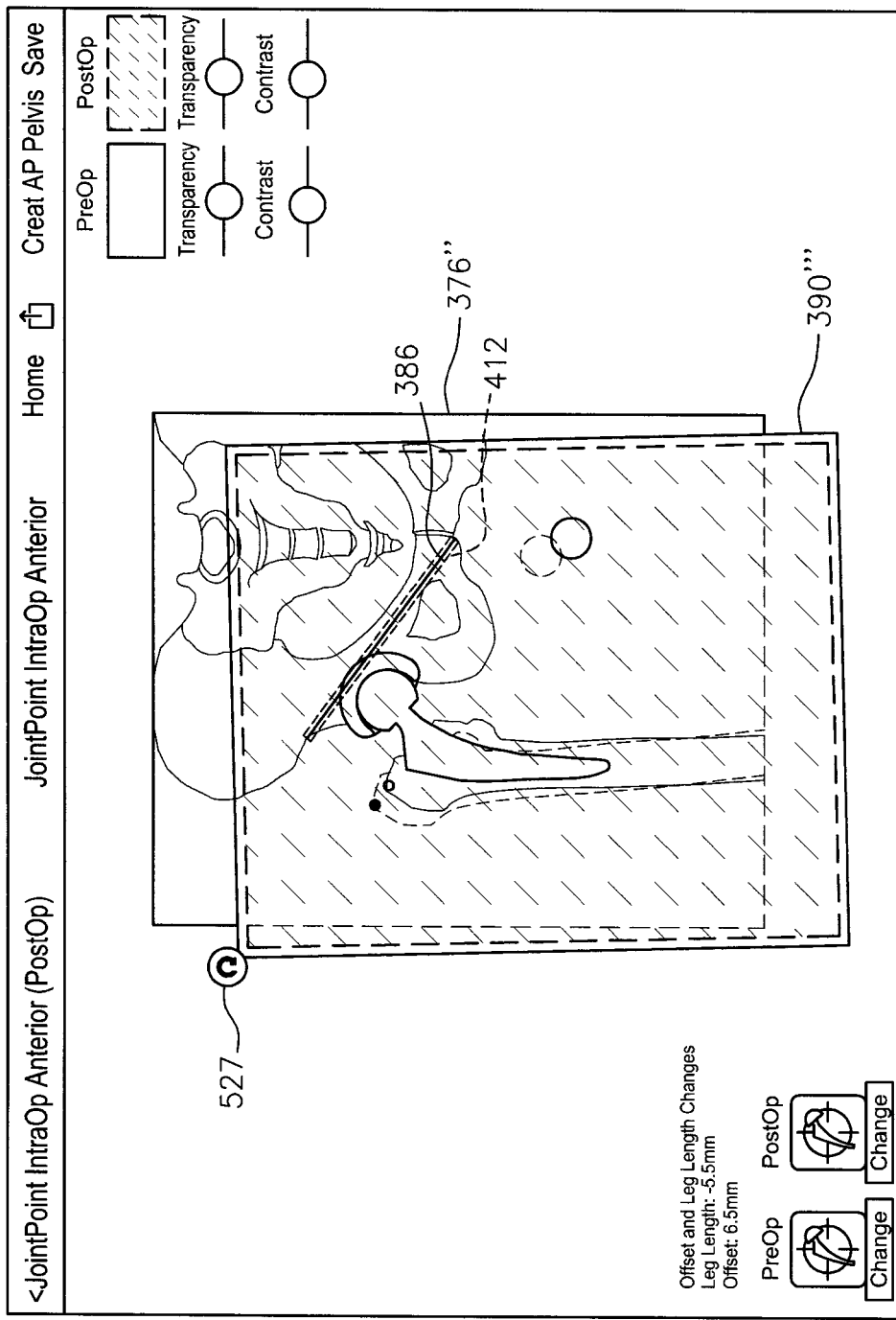
FIG. 12 is an overlay image showing the right-hand, intra-operative image of FIG. 11 superimposed and aligned with the left-hand, pre-operative image.

FIG. 12 is an overlay image showing the right-hand, intra-operative, PostOp image 390''' of FIG. 11 superimposed and aligned with the left-hand, pre-operative PreOp image 376". In this construction, soft button icons for selectively changing PreOp image 376" and/or PostOp image 390" are provided at the lower left-hand portion of the screen.

Note that "PostOp" as utilized herein typically indicates post-insertion of a trial prosthesis during the surgical procedure, and is preferably intra-operative. The PostOp image can also be taken and analysis conducted after a "final" prosthesis is implanted. "PreOp" designates an image preferably taken before any surgical incision is made at the surgical site. In some situations, the image is taken at an earlier time, such as a prior visit to the medical facility and, in other situations, especially in emergency rooms and other critical care situations, the "PreOp" image is taken at the beginning of the surgical procedure. A ball marker BM, FIG. 5, is shown but not utilized for alignment because ball markers can move relative to the patient's anatomy. Further PreOp and PostOp icons are provided in certain screen views to adjust viewing features such as contrast and transparency. Preferably, at least one icon enables rotation in one construction and, in another construction, "swaps" the images so that the underlying image becomes the overlying image, as discussed in more detail below.

Additional icons and reference elements are provided in some constructions, such as described in the parent application. One or more of these "virtual" items can be removed or added to a screen view by a user as desired by highlighting, touching or clicking the "soft keys" or "soft buttons" represented by the icons. In certain embodiments, one or more of the icons serves as a toggle to provide "on-off" activation or de-activation of that feature. Characters or other indicia can be utilized to designate image number and other identifying information. Other useful information can be shown such as Abduction Angle, Offset Changes and Leg Length Changes, as discussed in more detail below. Optional user adjustment can be made by touching movement control icon 527, FIG. 12, also referred to as a "rotation handle".

In certain constructions, image recognition capabilities provide "automatic", system-generated matching and alignment, with a reduced need for user input. Currently utilized image recognition provides automatic detection of selected items including: the spherical ball marker frequently utilized in preoperative digital templating; the acetabular cup in digital templates and in trial prosthetics; and the Cobb Angle line, also referred to as abduction angle.

Figure 13:
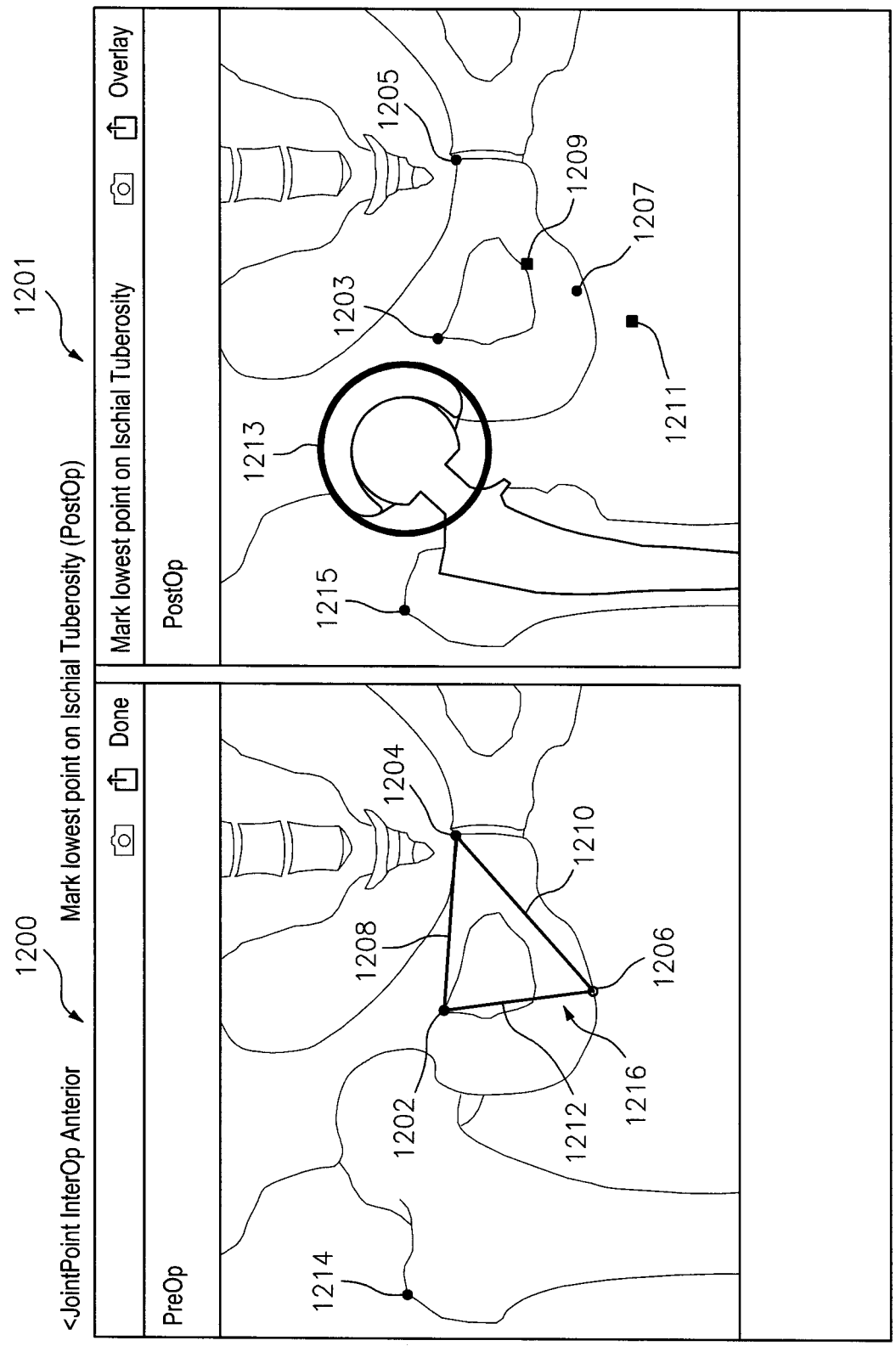
FIG. 13 is an image similar to FIG. 11 with points marking the lowest point on the ischial tuberosity and points marking the obturator foramen and top of the pubic symphysis in both pre- and intra-operative views.
Figure 14:
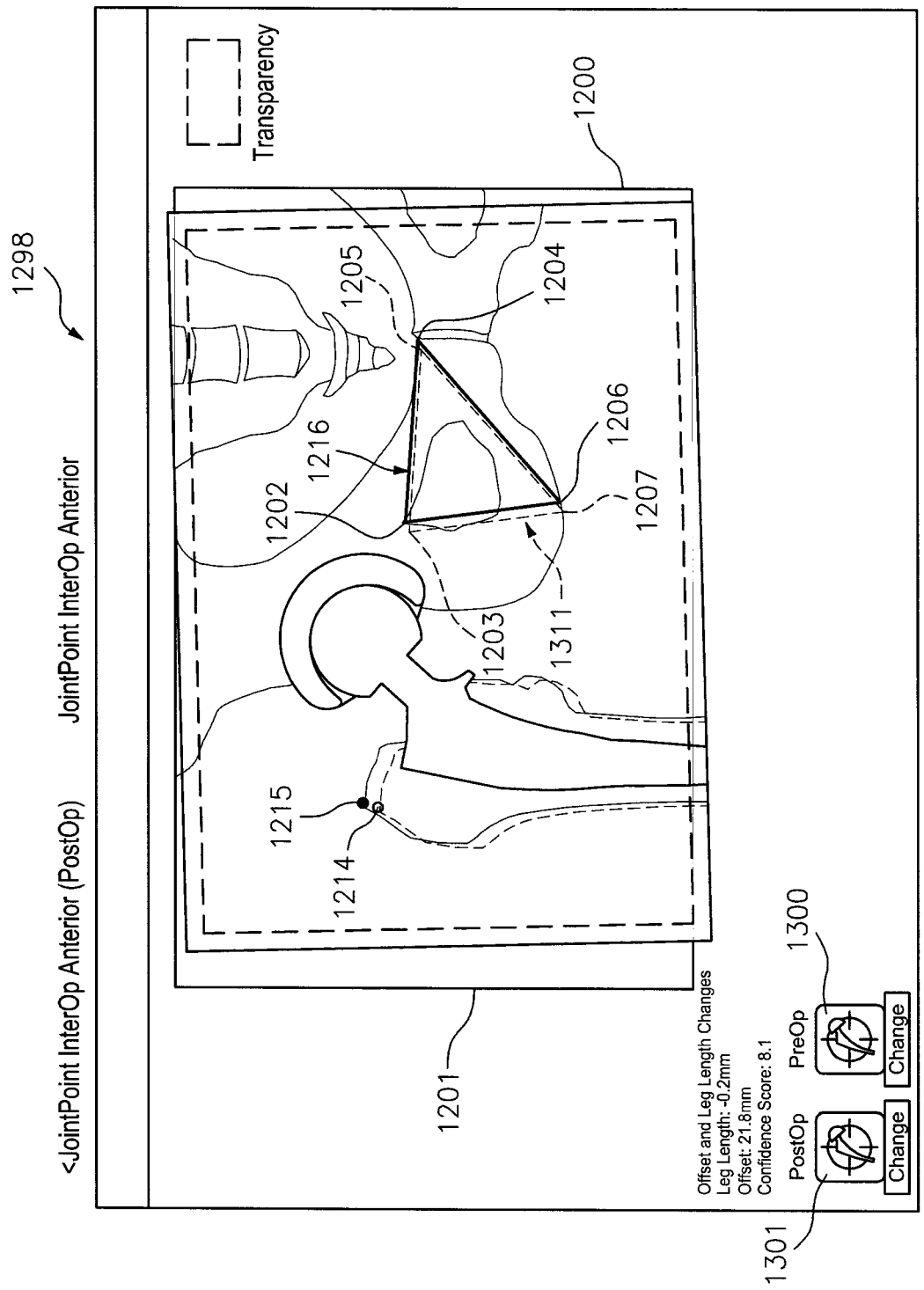
FIG. 14 is an overlay image showing the right-hand, intra-operative image of FIG. 13 superimposed and aligned with the left-hand, pre-operative image utilizing triangular stable bases.

In another construction, more than two points are generated for the stationary base for each image, such as illustrated in FIG. 13 for a preoperative image 1200 and a postoperative image 1201, and in FIG. 14 for a combined overlay image 1298 of the preoperative image 1200 and the postoperative image 1201 of FIG. 13. Similar locations on the pelvis in each image are selected to generate the points utilized to establish a stationary base for each image. In image 1200, for example, a first point 1202 is generated on an upper corner of the obturator foramen or at the pelvic tear drop, a second point 1204 is generated at the top or superior portion of the pubic symphysis, and a third point 1206 is generated at the lowest or inferior point on the ischial tuberosity. Lines 1208, 1210 and 1212 are drawn connecting those points to generate a visible stationary base triangle 1216 on image 1200. Also shown is a point 1214 on the greater trochanter. In postoperative image 1201, first and second points 1203 and 1205 correspond with first and second points 1202 and 1204 in image 1200. A third point 1207 is shown in image 1201 between reference squares 1209 and 1211 in the process of a user selecting the lowest point on the ischial tuberosity to correspond with third point 1206 in image 1200. The user is prompted by "Mark lowest point on Ischial Tuberosity" in the upper portion of image 1201. Also shown is a circle 1213 around the acetabular component and a point 1215 on the greater trochanter.

Establishing at least three points is especially useful for determining rotational differences between images. Overlay image 1298, FIG. 14, shows the three points 1202, 1204 and 1206 of preop image 1200, forming the visible preop stationary base triangle 1216, which is positioned relative to the corresponding three points 1203, 1205 and 1207 of postop image 1201, forming a visible postop stationary base triangle 1311 overlaid relative to triangle 1216 in FIG. 14. A "best fit overlay" can be created using these points by identifying the centroid of the polygon created by these point and rotating the set of points relative to one another to minimize the summation of distance between each of the related points. In this construction, scaling of the two images may be performed by this same set of points or, alternatively, a separate set of two or more points may be utilized to scale the two images relative to each other. Clicking on a PreOp soft-button icon 1300 and a PostOp icon 1301 enable a user to alter positioning of images 1200 and 1201, respectively, within image 1298 in a toggle-switch-type manner to selectively activate or de-activate manipulation of the selected feature. One or more points of a stationary base may be shared with points establishing a scaling line. Preferably, at least one landmark is selected that is spaced from the stationary base points to increase accuracy of overlaying and/or comparing images.

Also illustrated in FIG. 14 are "Offset and Leg Length Changes" with "Leg Length: −0.2 mm", "Offset: 21.8 mm" and "Confidence Score: 8.1". A confidence ratio that describes the quality of fit can be created by comparing the overlay area of the two triangles relative to the size of the overall polygon formed by the two triangles, including the non-overlapping areas of each triangle. Abduction angle and anteversion calculations are described in the parent application in relation to FIGS. 55-59.

Alternative constructions may alternatively apply absolute scaling to the preoperative and intraoperative images directly in each image, and without the need for a stationary base. For example, each image may be scaled by a ball marker or other scaling device, known magnification ratios of a radiographic device, or direct measurements of anatomical points (such as a direct measurement, via calipers, of the extracted femoral head, which can be used to scale the preoperative image).

Alternative constructions may also replace the "stationary base" with various other techniques that could be used to scale and align the preoperative and intraoperative images relative to one another. One example of such a construction would involve overlaying two images and displaying them with some transparency so that they could both be viewed on top of one another. The user would then be prompted to rotate and change their sizing, so that the pelvic anatomy in the two images were overlaid as closely as possible.

Figure 15:
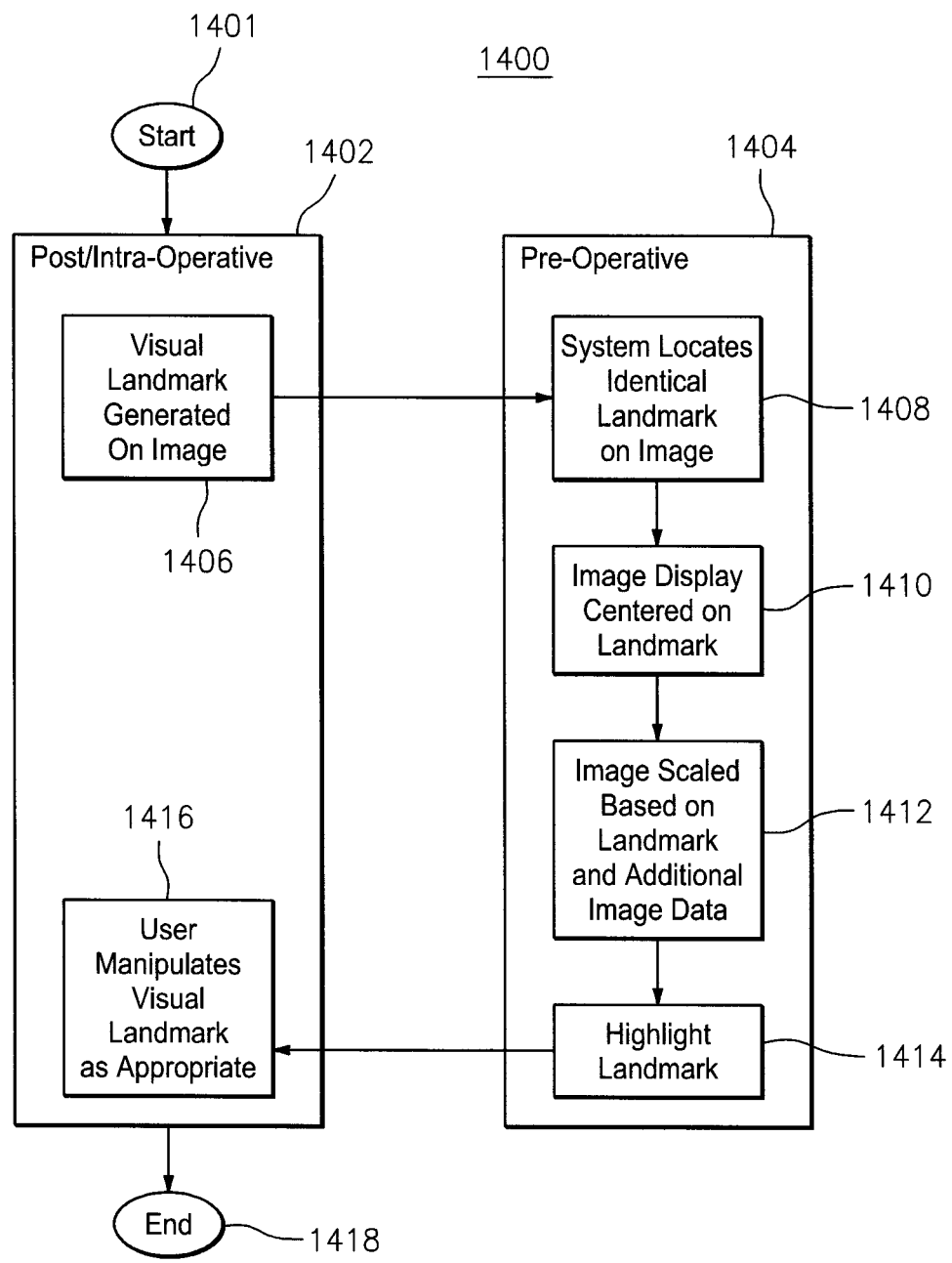
FIG. 15 is a schematic combined block diagram and flow chart of an identification guidance module utilized according to aspects of the present invention.

In some constructions, a guidance system is provided to adjust the viewing area of one image on a screen to track actions made by a user to another image on the screen, such as to focus or zoom in on selected landmarks in each image. This feature is also referred to as an automatic 'centering' function: as a user moves a cursor to 'mark' a feature on one image, such as placing a point for a landmark or a stationary base on an intraoperative image, the other image on the screen is centered by the system to focus on identical points of interest so that both images on the screen are focused on the same anatomical site. FIG. 15 is a schematic combined block diagram and flow chart of an identification guidance module 1400 utilized in one construction to assist a user to select landmarks when comparing a post- or intra-operative results image, box 1402, with a reference image, box 1404. The module is initiated with a Start 1401 and terminates with an End 1418. When a visual landmark is added to a post-operative image, box 1406, the module 1400 locates all landmarks "l" on the pre-operative reference image, box 1408, and calculates the visible area "v" within the pre-operative image in which to scale, such as by using Equation 1:

$$v = [\max x(l) - \min x(l), \max y(l) - \min y(l)] \quad \text{EQ. 1}$$

The identical landmark on the pre-operative image is located and its center-point "c" is determined, box 1410. The identical landmark on the pre-operative image is highlighted in one construction to increase its visual distinctiveness, box 1414. The pre-operative image is centered, box 1410, and scaled, box 1412, such as by utilizing the following Equations 2 and 3, respectively:

$$\text{Center} = c - (v)(0.5) \quad \text{EQ. 2}$$

$$\text{Scale} = i/v \quad \text{EQ. 3}$$

The user manipulates one or more visual landmarks in the results image, box 1416, as desired and/or as appropriate. In some constructions, the user manually ends the guidance activities, box 1418 and, in other constructions, the system automatically discontinues the guidance algorithm.

In certain constructions, image recognition capabilities provide "automatic", system-generated matching and alignment, with a reduced need for user input. Currently utilized image recognition provides automatic detection of selected items including: the spherical ball marker frequently utilized in preoperative digital templating; the acetabular cup in digital templates and in trial prosthetics; and the Cobb Angle line, also referred to as abduction angle.

Figure 16:
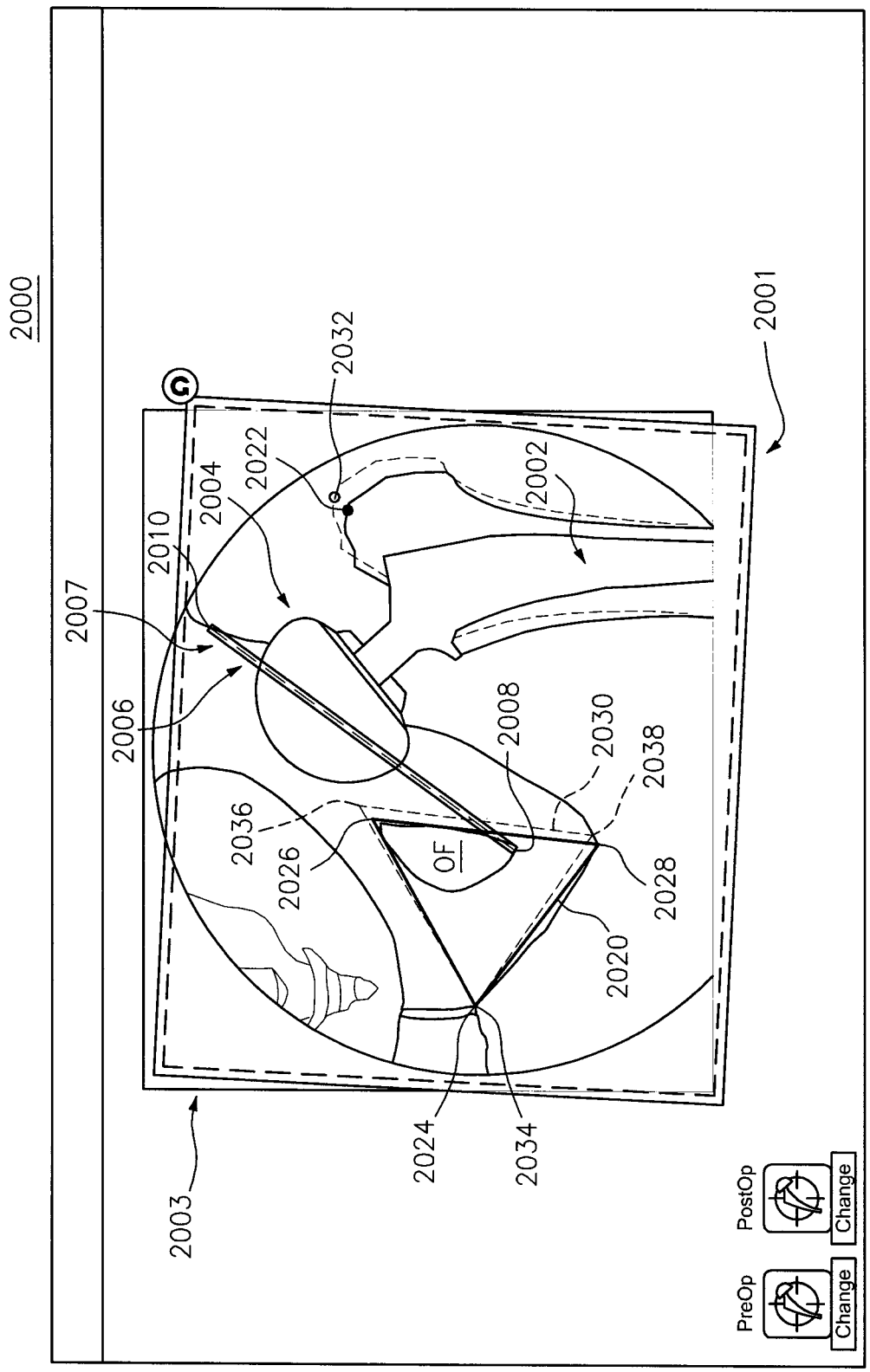
FIG. 16 is an image of a trial implant in a hip with the acetabular component transacted by a stationary base line and with two error analysis triangles.

FIG. 16 is an overlay image 2000 of a preoperative hip image 2001 and an intraoperative hip image 2003 having a trial implant 2002 in a hip with the acetabular component 2004 transacted by stationary base lines 2006 and 2007 extending between a first point 2008 on the obturator foramen OF and a second point 2010 on the anterior inferior iliac spine AIIS of the ileum. Also shown are two error analysis triangles 2020 (solid lines) and 2030 (dashed lines). Circles 2022 and 2032 in this construction represent a landmark point on the greater trochanter in images 2001 and 2003, respectively. Image 2000 is a representation of pre-operative and intraoperative hip images 2001 and 2003 overlaid according to stationary base lines 2006 and 2007, respectively. Three identical pelvic points 2024, 2026, 2028 and 2034, 2036, 2038 in images 2001 and 2003, respectively, have been identified, with a system such as system 200, FIGS. 4C-4F in the parent application, generating triangles 2020 and 2030 for each image as represented by FIG. 16. The triangles 2020 and 2030 can be visually compared to analyze the error in the anatomic area containing the stationary bases which, in this case, is the pelvis. A numerical confidence score or other normalized numeric error analysis value may also be calculated and displayed in the system by calculating the distance between points, comparing them to the length of the triangle vectors, and then normalizing the data, possibly using a log or other such nonlinear algorithm. The visual display and/or numerical confidence score provides efficacy analysis in the construction. In other words, error analysis and correction is provided in some constructions for at least one image, such as providing a confidence score or other normalized numeric error analysis, and/or a visual representation of at least one error value or error factor, such as relative alignment of one or more geometric shapes, e.g. triangles, or symbols in two or more images.

In some constructions of the various alternative systems and techniques according to the present invention, visual and/or audible user instructions are sequentially generated by the system to guide the user such as "Draw line along Pubic Symphysis". Guidance for surgery utilizing other types of implants, and for other surgical procedures, including partial or total knee or shoulder replacements and foot surgery as well as wrist surgery, will occur to those skilled in the art after reading this disclosure. Also, other types of medical imaging using energy other than visible light, such as ultrasound, may be utilized according to the present invention instead of actual X-rays. Moreover, if a computer interface tool, such as a stylus or light pen, is provided to the user in a sterile condition, than the user can remain within a sterile field of surgery while operating a computing device programmed according to the present invention.

The term "vector" is utilized herein with the standard meaning of an Euclidean vector having an initial point or "origin" and a terminal point, representing magnitude and direction between the origin and the terminal point. The system then positions an acetabular component template or representative digital annotation, such as a digital line or digital circle, in the preop image by replicating this vector.

Hip- and femur-related constructions of the present system and method calculate intraoperative changes in offset and leg length using a reference image, also referred to as a "preop image", and an intraoperative image, also referred to as a "postop image" or an "intraop image". To accomplish this, one construction of the system requires two consistently scaled images that are overlaid and aligned according to the stationary anatomic region (such as the pelvis), the generation of at least one landmark point on the non-stationary, articulating anatomic region (such as the femur) in both images, a mechanism to identify the difference in femoral angle of the femur relative to the pelvis between the images, a mathematical correction module that adjusts for differences in the articulating femur in each image relative to the stationary pelvis and, finally, a calculation module that uses this input to calculate intraoperative changes in offset and leg length. As utilized herein, the term "femoral angle" refers to the orientation of the longitudinal axis of the femur relative to the pelvis; a "difference in femoral angle" is described in more detail below in relation to FIG. 21. The system may optionally include an error analysis module that identifies and analyses potential error in the system.

As described in more detail below in relation to FIGS. 17-23, an 'Image Overlay' process according to the present invention begins in some constructions by acquiring (i) at least one of a preoperative ipsilateral or an inverted contralateral image ("preop image" or "reference image"), and (ii) an intraoperative image ("intraop image"). The system generates at least one landmark point on the non-stationary femur in both images (such as identification of a consistent point on the greater trochanter in both images), generally performed with user guidance. Optionally, the system will generate at least one error point on the pelvis in both images to provide error analysis. If the images have not been previously scaled and aligned, the system will scale and align them using one of a plurality of techniques. One of the images is then overlaid according to the pelvic anatomy in both images.

In some constructions, the system identifies points that can be used to analyze possible error in the images relative to each other. The system additionally performs a series of steps to calculate any deviation in alignment of the non-stationary femur relative to the pelvic anatomy between the preop and intraop images. The system then creates an overlay of the preop and intraop image, taking into consideration and correcting for the effect of any difference in femoral angles between the two images as the system compares the relative position of the generated femoral landmark points. Finally, the system analyses the difference between the landmark points, including a correction for femoral alignment differences, and uses this data to calculate intraoperative change in offset and leg length.

Figure 17:
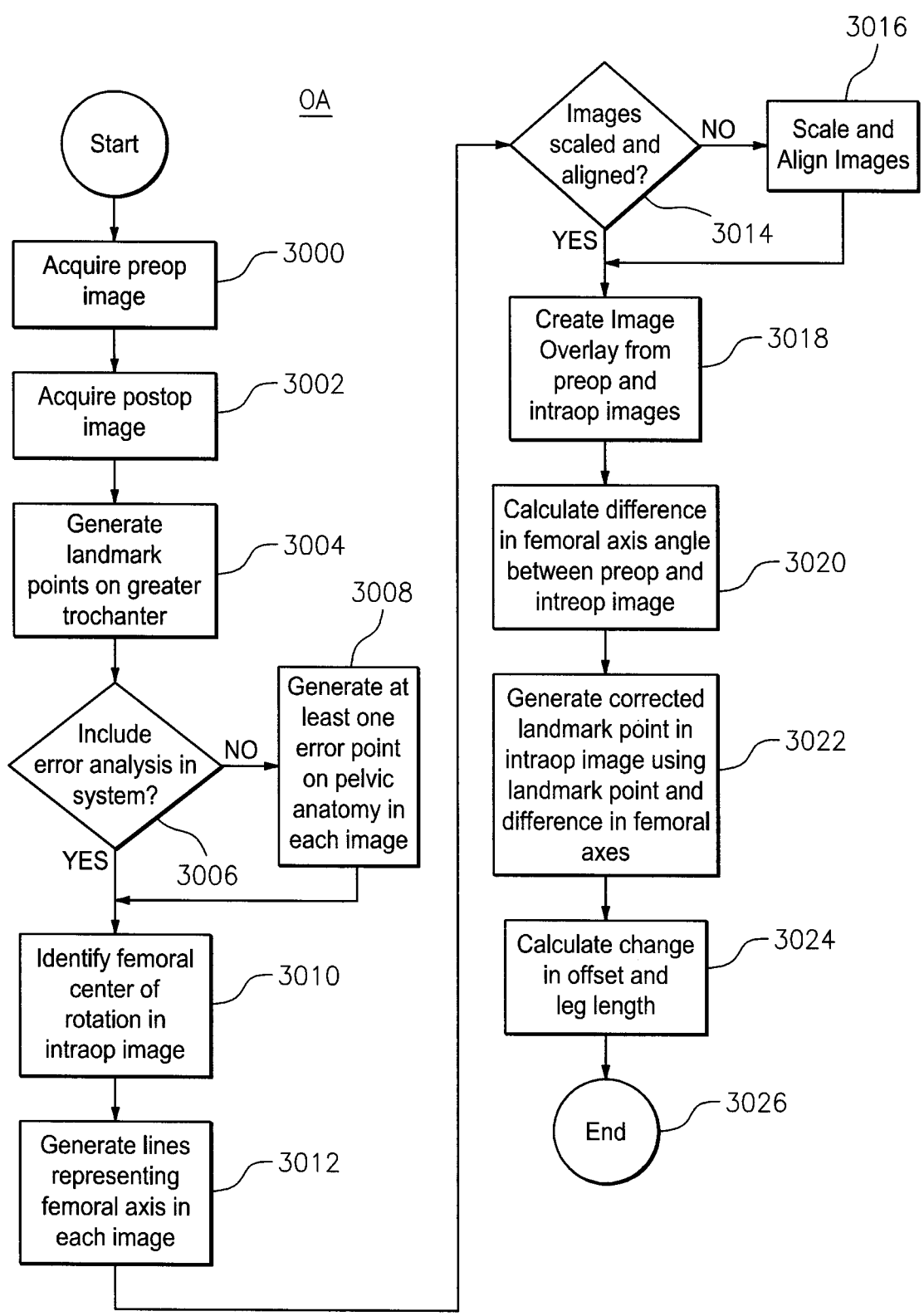
FIG. 17 is a flowchart showing the use of an 'Image Overlay' technique to calculate a postoperative change in offset and leg length according to an aspect of the present invention.

In one construction, the process begins in the flowchart OA in FIG. 17 by acquiring, step 3000, either a selected preoperative ipsilateral image, or a selected inverted contralateral image. Whichever image is selected is referred to herein as a "first, reference image" or "preop image". The process continues with acquisition of the intraop hip image, step 3002. Image acquisition in steps 3000 and 3002 is performed by the Image Capture module 3030, also referred to as an Image Selection Module, of overlay analysis system 3028, FIG. 18. Acquisition of these images can be performed in a variety of ways, such as a direct connection to a c-arm fluoroscopy unit, file upload, or similar techniques. Implementations that operate on a mobile device such as an iPad, or other platforms that similarly integrate a camera device, may also acquire the images in steps 3000 and 3002 by prompting the user to take a picture of the images using the device camera. If an inverted contralateral image is used as a 'preop' image, the contralateral image may be acquired and then inverted within the software, or otherwise it may be flipped in another system and then input to image capture module 3030. Screen view 3050, FIG. 19, shows preoperative image 3052 and intraoperative image 3070, referred to by labels 3053 and 3071 as "PreOp" and PostOp" images, respectively.

Figure 18:
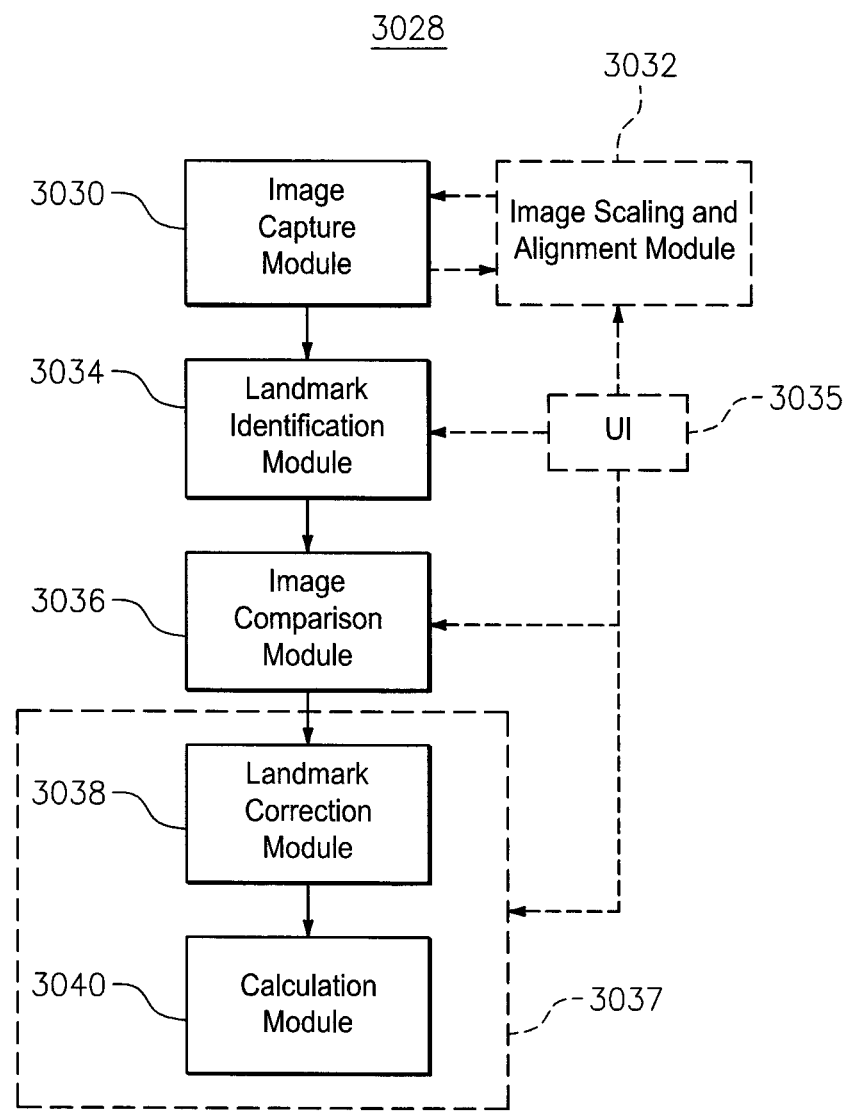
FIG. 18 is a schematic diagram of an Image Analysis System according to the present invention.

The method continues in step 3004, FIG. 17, with Landmark Identification Module 3034, FIG. 18, identifying at least one point on the femoral anatomy in both the preop and intraop images. Landmark Identification Module 3038 and Calculation Module 3040 can be considered as components of an Analysis Module 3037, shown in dashed lines. In a preferred construction, a point in each image will be placed on the greater trochanter, a particularly useful landmark point because it is easily identifiable and because the anatomy is relatively insensitive to deviations in image acquisition. Alternatively, the point may be placed on the lesser trochanter or another identifiable femoral landmark. However, consistent point placement on the lesser trochanter is more susceptible to error originating from deviations in image acquisition angle based on its 3-dimensional anatomy. In various constructions, the user is either prompted to identify the point on the femoral anatomy, or otherwise the system auto-identifies the point or set of points using image recognition or other technology and then allows the user to modify the point placement.

FIG. 5, described above, is an image 376 of the right side of a patient's hip prior to an operation and showing a marker 378, bracketed by reference squares 377 and 379, placed by a user as guided by the system, or placed automatically via image recognition, on the greater trochanter as a landmark or reference point, such as indicated in Landmark Identification Module 3034, FIG. 18. Reference squares 377 and 379 enable the user to position the marker 378 on touchscreen devices, such as an iPad, without the user's fingers obscuring the position of the marker 378.

Figure 19:
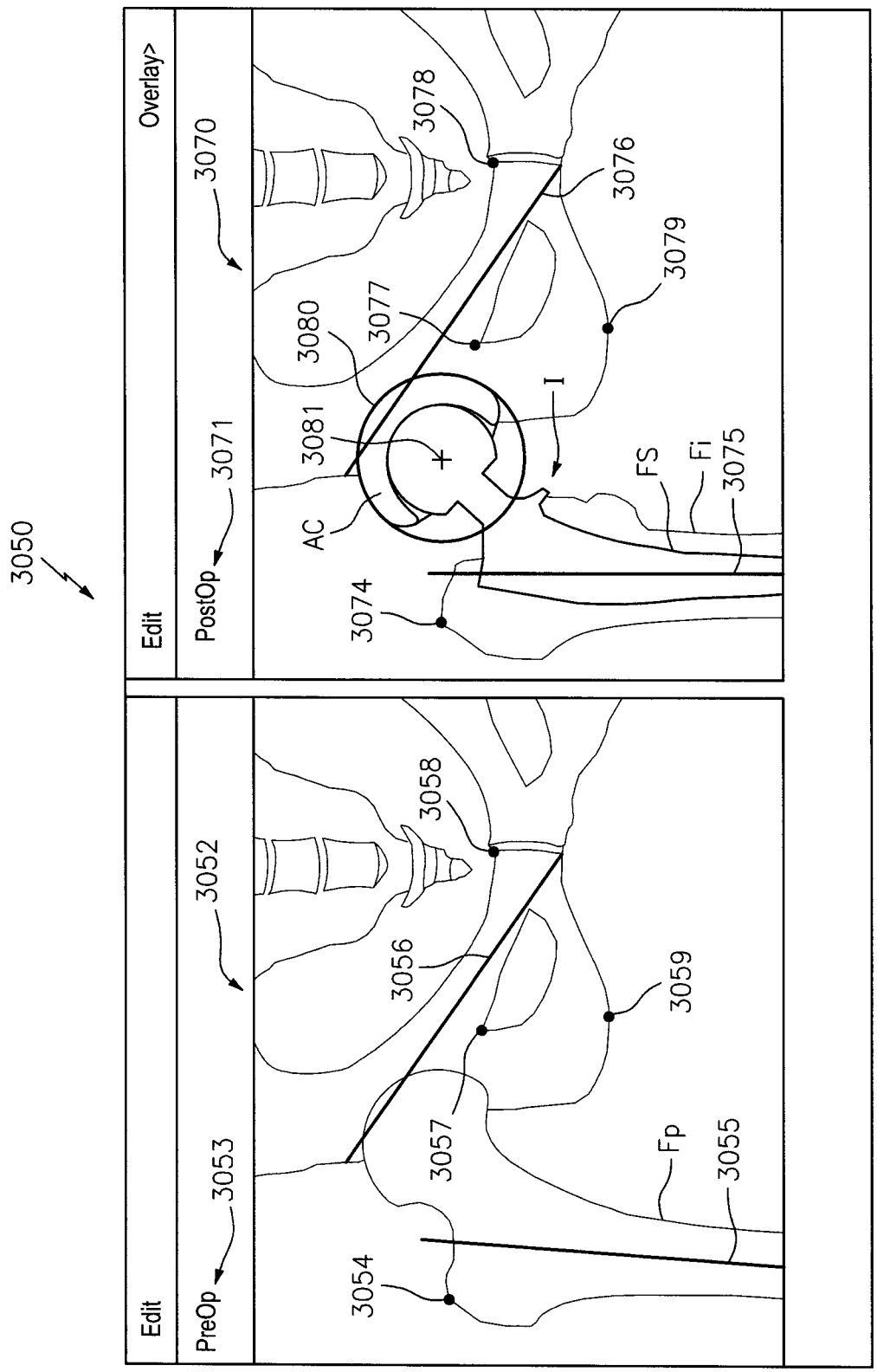
FIG. 19 is a schematic screen view of a preoperative image and an intraoperative image positioned side by side with digital annotations marking anatomic landmarks and stationary points on the images.

In a similar manner, reference landmark point 3054 and intraoperative landmark point 3074, FIG. 19, are placed on the greater trochanter of the femur Fp in PreOp image 3052 and of femur Fi in PostOp image 3070, respectively. Also shown in PreOp image 3052 are a femoral axis line 3055 and a pelvic reference line 3056, tear drop point 3057, pubic symphysis point 3058, and ischial tuberosity point 3059.

Further shown in PostOp image 3070, FIG. 19, are acetabular cup AC and femoral stem FS of an implant I, a femoral axis line 3075 and a pelvic reference line 3076, tear drop point 3077, pubic symphysis point 3078, and ischial tuberosity point 3079. A circle 3080 has been drawn around acetabular cup AC as described in more detail below.

In step 3006, FIG. 17, the Landmark Identification Module 3034, FIG. 18 asks via User Interface UI, shown in phantom as box 3035, whether the user wants to include error analysis in the system output. If yes, Module 3034 prompts the user, in Step 3008, to identify a set of anatomic points on the stationary pelvis in both the preop and intraop images. While a minimum of only one point is required to provide error analysis in the system, the system preferably generates at least three points on the pelvis, such as points 3057, 3058 and 3059 in PreOp image 3052, FIG. 19, and points 3077, 3078 and 3079 in PostOp image 3070. The user positions each point on the pelvis in some constructions but, in preferred constructions, automated algorithms of a system according to the present invention initially place the points in appropriate positions on the pelvic anatomy. If pelvic reference lines, as described in more detail below, are used to align and scale the preop and intraop images, the points selected for error analysis should be independent of the points used to create the pelvic reference lines. Ideal points will also be identifiable, such as a discernible point on the pelvic teardrop, ischial tuberosity and pubic symphysis.

In Step 3010, the Landmark Identification Module 3034, FIG. 18, identifies the approximate femoral center of rotation in the intraop image; this center of rotation information assists correction for deviations in femoral positioning between the preop and intraop images. In a preferred construction, Landmark Construction Module 3034 identifies this point by placing a digital circle so that it overlays the boundary of the acetabular component, as shown by digital circle 392 in FIG. 9 and by circle 3080 in FIG. 19. The system then identifies the midpoint of the circle, which approximates the center of rotation of the acetabular component and functions as the intraoperative femoral center of rotation.

Various constructions will accomplish step 3010 in different ways. In a preferred construction, the system may auto-detect the location of the digital circle by using image recognition to auto-detect the acetabular component in the intraoperative image, and then allow the user, via User Interface UI, box 3035, to adjust the size and position of the digital circle using navigation handles connected to the circle, such as navigation handle 527, FIG. 12, and by navigation handle 3099, FIG. 20. In another construction, the user estimates the approximate center of rotation by drawing or positioning a circle around the femoral head in the preoperative image, and utilizing the center of that circle as an estimate of the center of rotation.

As shown in FIG. 19, the PreOp image 3052 shows three error points 3057, 3058 and 3059 positioned on the base of the pelvic teardrop, the superior point on the pubic symphysis, and the inferior point on the ischial tuberosity, respectively. Similarly, points 3077, 3078 and 3079 are positioned on corresponding points in PostOp image 3070. These corresponding points will be used for error analysis in constructions that include error analysis as part of the system. Digital circle 3080 has been positioned around the acetabular cup AC of implant I, with a center-point represented by the crosshair 3081 that identifies the midpoint of the circle. This midpoint identifies the approximate femoral center of rotation after implant insertion.

In Step 3012, FIG. 17, the system begins the process of analyzing the difference in the femoral axis angles, relative to the pelvis, between the preop and intraop images. In a preferred construction, the system accomplishes this by generating digital lines to identify the longitudinal axis of the femurs in both images, such as femoral axis lines 3055 and 3075, FIG. 19, and calculating any angle difference between them as described in more detail below in relation to FIG. 21. Landmark Identification Module 3034, FIG. 18 guides the user to generate a line that identifies the longitudinal axis of the femur in both the preop and intraop images. First, the system generates a digital line in the preop image to identify the femoral axis, and the system provides the ability to adjust the line location so that it can identify the angle of the femur in the preop image. Then, the system generates a digital line in the intraop image to identify the femoral axis in the intraop image, again allowing for user adjustment. Preferred constructions of this system will attempt to auto-identify the femoral axis in this step using image recognition and known data, and place the digital lines accordingly. The system then provides the functionality for the user to further manipulate these lines.

FIG. 6, described above, is an image 376' similar to FIG. 5 showing a reference line 380, bracketed by reference squares 381, 382, 383 and 384, drawn on the preop image to represent the longitudinal axis of the femur. Reference lines 381, 382, 383 and 384 can be manipulated to reposition the femoral axis line. FIG. 10, described above, is a schematic screen view with a reference line 406 drawn on the intraoperative femur in the right-hand view 390", guided by reference squares 407, 408, 409 and 410. Reference lines 407, 408, 409 and 410 can be manipulated to reposition the femoral axis line. FIG. 19 again shows the positioned digital lines 3055 and 3075, placed in Step 3012, FIG. 17, that identify the femoral axis in the PreOp and PostOp images 3052 and 3070.

In step 3014, FIG. 17, the Image Capture Module 3030, FIG. 18 determines whether the preop and intraop images have been pre-scaled and aligned according to pelvic anatomy. Consistent scaling and alignment may be previously performed in this construction using a variety of approaches. For example, a software system residing on a digital fluoroscopy system may have been used to align and scale the images prior to image acquisition by this system. Alternatively, the images may already be scaled and aligned because the surgeon took images with the patient and radiographic system in identical position with a known magnification ratio.

If the images have not been either scaled or aligned, the system can scale, or align, or scale and align the images in optional step 3016. Consistent scale and alignment in this step is accomplished by the optional Image Scaling and Alignment Module 3032, FIG. 18, shown in dashed lines, which may accomplish these operations in various ways.

One method to accomplish consistent scaling and alignment is by using stationary bases (i.e. pelvic reference lines), along with identification and scaling of the acetabular cup in the intraop image, as visually illustrated in FIG. 11. In this approach, a line is drawn connecting two identical landmarks on the pelvis in both the preop and intraop images. Stationary base line 386 in FIG. 15 connects, in the preop image, a point on the anterior superior iliac spine to the inferior point on the pubic symphysis. Stationary base line 412 in FIG. 11 connects the identical two pelvic landmarks in the intraop image. The system can use these two lines to rotate the images so that the overlay lines are aligned at the same angle relative to the software screen. The images can additionally be scaled, relative to one another, by scaling one image relative to another so that the pixel distances between the stationary base lines in the two images are equivalent.

Finally, absolute scaling of the images can be achieved by scaling at least one image according to an object of known dimension.

FIG. 8 depicts the digital circle 392 that has been generated around acetabular component 394. The digital circle may be either generated using image recognition to identify the acetabular component, positioned by the user, or initially system-generated in an approximate location and then positioned by the user. The size of this component is known because the surgeon has placed it in the patient's femur. Therefore, the known size of the component, such as "50" mm, can be entered into the box following text "Size of Acetabular Component" located at the top of the intraop screen 390. The system uses this information to generate absolute scaling in the intraop image. Additionally, the preop image can be scaled in absolute measurements, according to this generated circle, once the preop image is scaled so that the pelvic reference lines in both images are of equivalent length in pixels.

FIG. 19 depicts the pelvic reference lines 3056 and 3076 that have been generated on identical points on the preop and intraop images 3052 and 3070 of the pelvis, allowing the system to align and scale the images according to the input. Alternative constructions may apply absolute scaling to other objects of known size in either the preop or intraop image. For example, scaling can be applied according to the preop image by drawing a digital line across diameter of the femoral head in the preop image, and entering the size in absolute terms. This absolute measurement is known during surgery because the surgeon traditionally extracts the femoral head and measures its size, using calipers, during hip arthroplasty.

Figure 20:
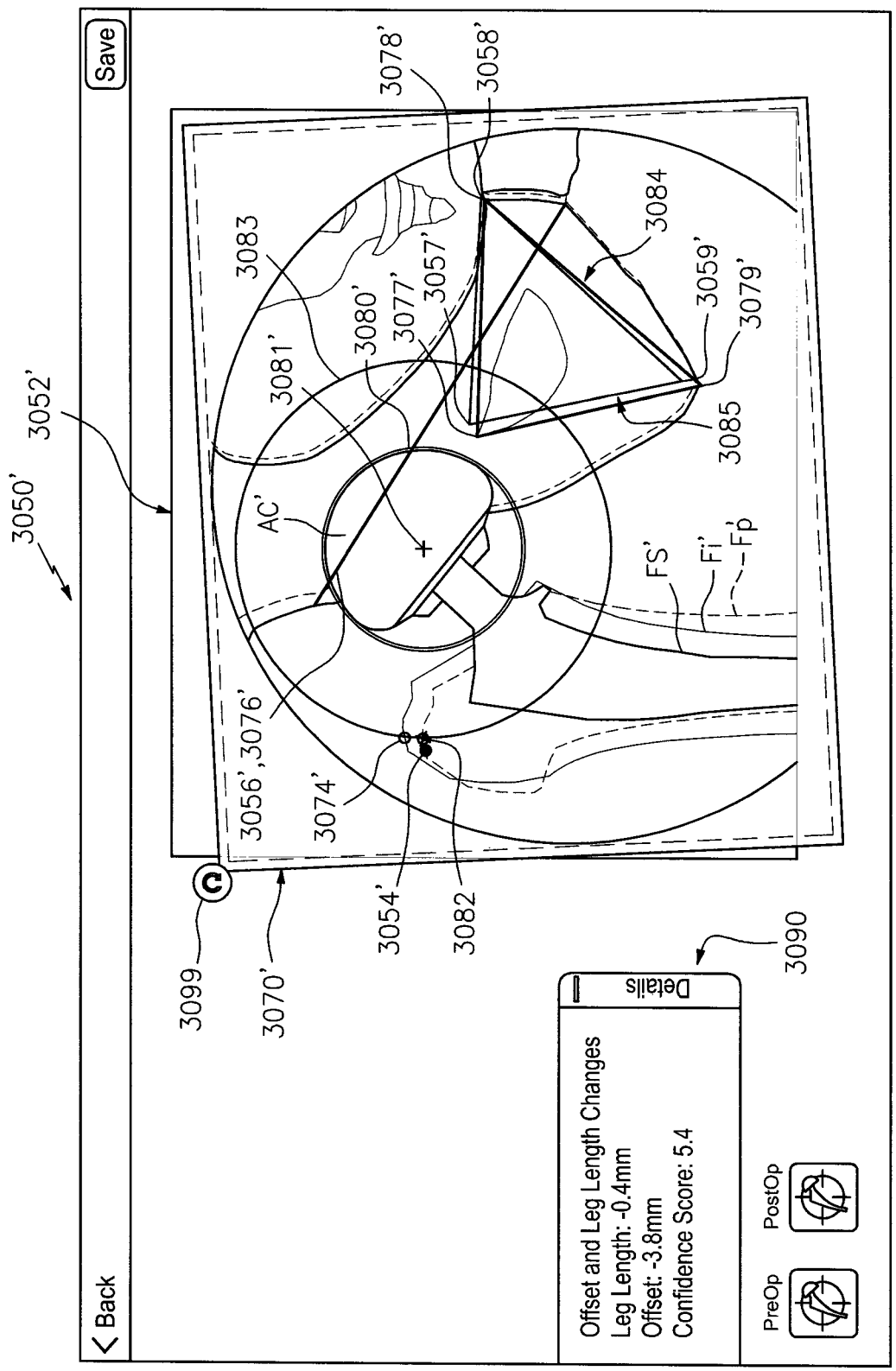
FIG. 20 is a schematic screen view of the preoperative image and intraoperative image of FIG. 19 overlaid according to pelvic anatomy with generated femoral landmark points and error analysis according to another aspect of the present invention.

The output of the scaling and alignment performed in step 3016, FIG. 17, is used to generate an overlay in step 3018, and therefore may be represented visually by depicting the updated scaling and alignment visually on the software screen, or otherwise may exclusively be calculated by the system to create the overlay in step 3018. In this construction of Step 3018, the Image Comparison Module 3036, FIG. 18 superimposes the preop and intraop images by aligning pelvic anatomy, with the images displayed with some transparency so that both can be visualized in the overlay, such as illustrated in FIG. 20. In a preferred construction the overlaid images will contain the identified femoral landmarks (generally placed on the greater trochanter) generated in step 3008 so that location differences between the two points can be visualized. The system will maintain the location of the generated greater trochanter points and the femoral axis lines, relative to the preop and intraop images, as the images are manipulated to create the image overlay.

The Image Comparison Module 3036 can align the images according to pelvic anatomy in a variety of ways in this step. In a preferred construction, the system will have previously guided the user in identifying at least two consistent points on the pelvic anatomy in both images. The Image Comparison Module 3036 then superimposes the images so that the stationary base lines are positioned identically. In other words, the images are scaled, aligned, and superimposed according to the stationary bases drawn across consistent points on the pelvis in each image. The Image Comparison Module will move and scale all digital annotations in tandem with the underlying image so that they remain affixed to the underlying image. This includes positioning of the femoral and pelvic landmark annotations, the identified center of rotation of the femur, pelvic reference lines, the femoral axis lines, and any other annotations used in various constructions.

Alternative constructions obviate the need for the use of the pelvic reference lines. In one alternative construction, the system uses image recognition technique to auto-identify the pelvic anatomy and overlay the images based on the image recognition, then the user is presented with the option to manually manipulate the resulting overlay. In another alternative, the user will be guided to manually position the images so that the pelvic anatomy matches. The system in this method will provide the user with the ability to manipulate both the position of each of the images as well as adjust the magnification so that the pelvic anatomy can be superimposed on the overlay. Alternative systems will rely on hardware implementations and stationary cameras to obviate the need for a digital line, image recognition, or user manipulation whatsoever to create the overlay. In these instances, the external system may provide a known magnification ratio and the consistent patient positioning that would be required to create the image overlay without the use of pelvic reference lines or similar technique.

Differences between the preop and intraop positioning of the femur, relative to the pelvis, creates a challenge in comparing the relative location of a femoral landmark such as a greater trochanter because a change in leg position alters the vector between the two femoral landmarks in the overlay. In Step 3020, FIG. 17, the Landmark Correction Module 3038, FIG. 18 calculates any existing difference between the preop and intraop femoral axis angles. The terms "femoral angle" and "femoral axis angle" refer to the orientation of the longitudinal axis of the femur. If, for example, the preop and intraop femoral axis lines generated in step 3012 vary by eight degrees, the difference calculated in step 3020 will be eight degrees.

In Step 3022, FIG. 17, Landmark Correction Module 3038, FIG. 18 uses data gathered in previous steps to generate an additional "corrected" or "phantom" landmark point that accounts for differences in femoral position between the preop and intraop images. A corrected landmark point 3082 is shown in FIG. 20, positioned along circle 3083 from intraoperative landmark point 3074', which is similar to corrected landmark point 3116, FIG. 21, along circle 3124 as described in more detail below.

To generate the corrected landmark point, the module first calculates $\text{angle}_{femur}$, which is the angular difference between the longitudinal axes of the femur in the preoperative and intraoperative images, respectively, also referred to as the preop and intraop femoral axis lines in the overlay. This technique is shown schematically in FIG. 21 for angle α, arrow 3108, between longitudinal axis lines 3104 ("L1") and 3106 ("L2"). The system incorporates this with the femoral or acetabular center of rotation 3102 ("R1"), $(X_{origin}, Y_{origin})$ in the intraop image, previously identified in step 3010, FIG. 17, and the greater trochanter point 3110 ("p1"), $(X_{troch}, Y_{troch})$ in the intraop image. The system uses the following formulas to calculate the corrected landmark "phantom" point 3116 ("p3"), $(X_{phantom}, Y_{phantom})$ in Equations 4 and 5:

$$X_{phantom} = (X_{troch} - X_{origin}) *_{cosine} (\text{angle}_{femur}) - \qquad \text{EQ. 4}$$
$$(Y_{troch} - Y_{origin}) *_{sine} (\text{angle}_{femur}) + X_{origin}$$

$$X_{phantom} = (X_{troch} - X_{origin}) *_{sine} (\text{angle}_{femur}) + \qquad \text{EQ. 5}$$
$$(Y_{troch} - Y_{origin}) *_{cosine} (\text{angle}_{femur}) + Y_{origin}$$

A vector "v", line 3118, is extended from the preoperative landmark point 3112 ("p2") to corrected landmark point 3116. Right triangle "legs" 3120 and 3122 are utilized to estimate offset and leg length, respectively. Leg 3122 is generally parallel to preoperative femoral axis 3104 in this construction. The Acetabular circle 3100 ("c1") assists in locating center of rotation 3102. Also shown in FIG. 21 are radius lines 3130 and 3132 which are also separated by angle α, arrow 3114.

As mentioned above, FIG. 20 is an "overlay" screen view 3050' of the intraop image 3070, FIG. 19, superimposed as PostOp image 3070' on the preoperative image 3052 as PreOp image 3052'. The two stationary base lines 3056 and 3076 of FIG. 19 are aligned exactly one on top of the other, represented as a single stationary base line 3056', 3076'. First error correction triangle 3084 is shown connecting intraoperative error point 3077' on the pelvic teardrop, point 3078' on the ischial tuberosity and point 3079' on the pubic symphysis, and a similar error correction triangle 3085 connects points 3057', 3058' and 3059', representing points 3057, 3058 and 3059 of preoperative image 3052, FIG. 19. Details window 3090 lists "Leg Length: −0.4 mm", "Offset: −3.8 mm" and "Confidence Score: 5.4" as described in more detail below.

Figure 21:
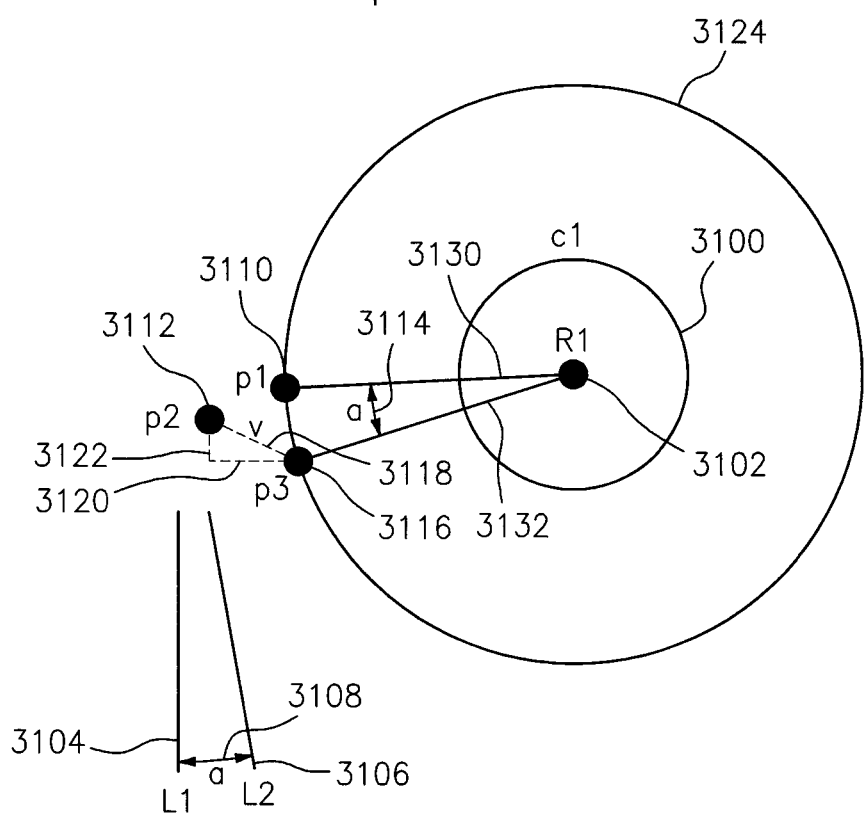
FIG. 21 is a schematic diagram showing generation of a corrected landmark point and analysis of offset and length differential according to the present invention.

Finally, in Step 3018, FIG. 17, the Calculation Module 3040, FIG. 18, calculates the change in leg length and offset by analyzing the vector between the greater trochanter point in the preop image and the calculated phantom point in the intraop image, such as illustrated in FIG. 21. To calculate leg length, the system calculates the distance between these two points along the femoral axis identified from the preop image, as identified by line 3122 in FIG. 21. To calculate offset, the system calculates the distance between the two points along the axis that is perpendicular to the femoral axis from the preop image, as identified by line 3120. A specific example of these calculations is given in Details window 3090, FIG. 20.

The "Confidence Score" listed in box 3090 relates to the two error triangles 3084 and 3085 as follows. The three points comprising each triangle enables the user to easily visualize any differences in pelvic anatomy in the overlay which may exist even after scaling and alignment. Although the stationary bases are completely matched one on top of the other, such as illustrated by single stationary base line 3056', 3076', the amount of deviation in the two error triangles 3084, 3085 can be visually inspected to appreciate potential error in the system, such as caused by one or more of parallax, differences in imaging vantage point of the three-dimensional skeletal anatomy, and/or by point placement within the system.

As an additional, optional step to quantify the differences between the placement of the two error triangles, the system provides a weighted "confidence score", ranging from 0.0 to 10.0 in this construction. In one implementation, the system finds the difference in an absolute scale between each of two corresponding points in the preop and postop images as overlaid. In some constructions, error in certain point pairs is assigned a weighting that is greater or lesser than for other error point pairs. As one example, identifying a consistent point on the ischial tuberosity may be difficult between images, so that particular point pair (labelled 3059' and 3079' in FIG. 20) can be weighted less, such as by "discounting" it by fifty percent. Finally, the weighted sum of numerical error among the error point pairs is converted to a single confidence score, such as "5.4" shown in display window 3090. The weighting is not necessarily linear. Further, a cut-off value can be provided beyond which the error is deemed to be too great to provide useful analysis; in one construction, the system then recommends that the user obtain an alternative intraoperative image to compare with the preoperative image, or with a contralateral image, to analyze according to the present invention.

Figure 22:
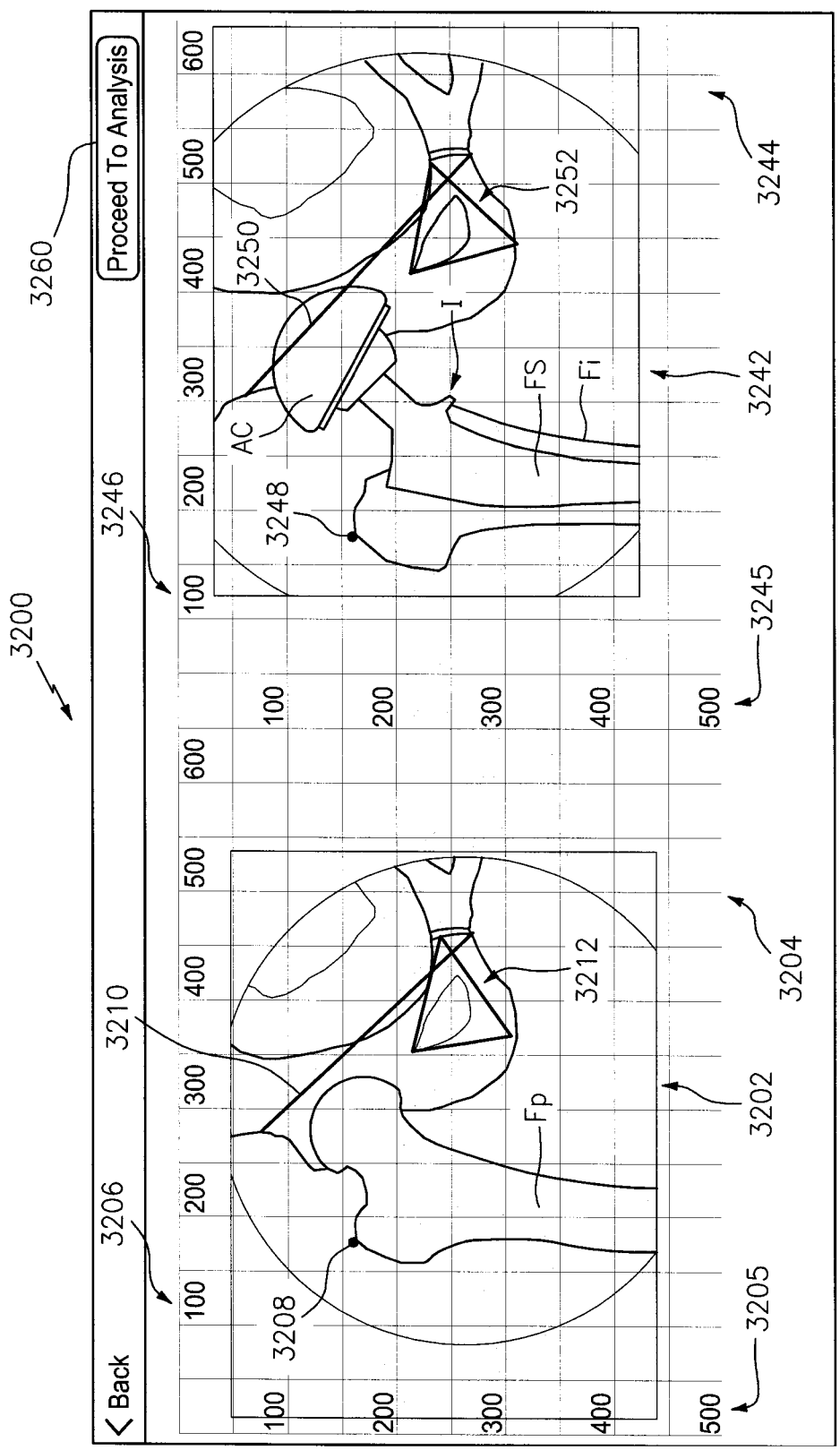
FIG. 22 is a schematic screen view of a preoperative image and an intraoperative image positioned side by side with a grid and digital annotations to mark anatomic landmarks and other features on the images according to certain aspects of the present invention.

Alternative constructions of this system and method will use different methods to determine the deviation between femoral angles in the preop and intraop images. For example, in one construction, the femoral angle can be analyzed by creating an image cut-out of one femur and superimposing it on top of the other at the original angle. The cut-out and underlying image may also be connected by the known femoral landmark, such as the greater trochanter, and be made to be immutable at that single landmark point. Then, at least one of the system and user may adjust the image cut-out so that the femoral bone precisely overlays the femoral bone in the superimposed image by pivoting about that landmark point. The system may accomplish this using image recognition or other automated algorithm that identifies the femoral bone or related femoral landmarks such as the greater trochanter landmark previously identified. Alternatively, the user may match the femoral bones by adjusting the superimposed image of the femur so that it matches the femur in the underlying image. The system may attempt to initially match the femoral bones and then provide the user the option to reposition the femur to improve the position. Finally, the system will calculate the deviation in angle between the two femurs by calculating the angle that the cut-out was adjusted, providing similar information In yet another construction, reference (preop) and intraop images are compared via a grid-type X-Y coordinate system without utilizing femoral angles, such as for preoperative images 3202, 3202' and intraoperative images 3242, 3242' in screen views 3200 and 3200' illustrated in FIGS. 22-23, respectively. The reference and intraoperative images are not actually digitally overlaid one on top of the other in this construction; instead, preop image 3202, FIG. 22, is overlaid with, or otherwise associated with, a grid 3204 having a Y-axis 3205 and an X axis 3306 with units "100, 200, . . . 500" as shown, with the origin in the upper left-hand corner of grid 3204. In a similar manner, intraop image 3242 is associated with a grid 3244 having a Y-axis 3245 and an X axis 3346, preop image 3202', FIG. 23, is associated with a grid 3204' having a Y-axis 3205' and an X axis 3306, and intraop image 3242' is associated with a grid 3244' having a Y-axis 3245' and an X axis 3346'.

Preop image 3202, FIG. 22, includes femur Fp with landmark point 3208 on the greater trochanter, and stationary base 3210 and error triangle 3212 on the pelvis. Intraop image 3242 includes femur Fi with implant I having femoral stem FS and acetabular cup AC. Intraoperative landmark point 3248 has been placed on the greater trochanter. Stationary base 3250 and error triangle 3253 have been placed on the pelvis.

Figure 23:
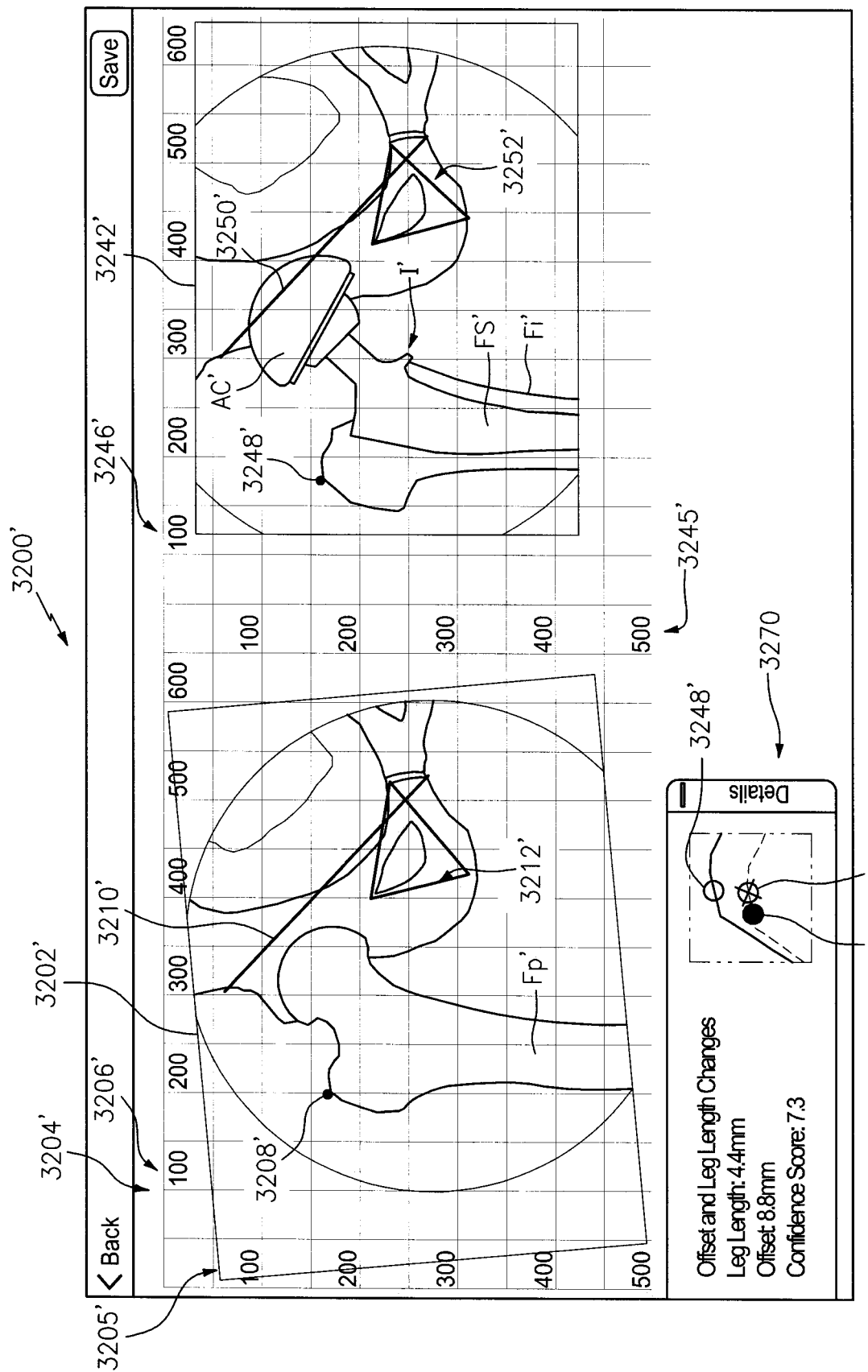
FIG. 23 is a schematic view similar to FIG. 22 after the preoperative image has been aligned with the intraoperative image.

Preop image 3202', FIG. 23, includes femur Fp' with landmark point 3208' on the greater trochanter, and stationary base 3210' and error triangle 3212' on the pelvis. Intraop image 3242' includes femur Fi' with implant I' having femoral stem FS' and acetabular cup AC'. Intraoperative landmark point 3248' is on the greater trochanter. Stationary base 3250' and error triangle 3253' have been placed on the pelvis.

After a user activates a "Proceed To Analysis" icon 3260, FIG. 22, the system aligns preop image 3202', FIG. 23, with intraop image 3242'. In this example, preop image 3202' has been "tilted" or rotated counter-clockwise relative to the initial position of preop image 3202 in FIG. 22 to represent alignment achieved using stationary base 3210' and 3250'. After both preop image and 3202' and 3242' have been aligned relative to each other, then a difference in position of one of the landmark points is determined, such as the shift of preop landmark point 3208, FIG. 22 to the aligned position of preop landmark point 3208', FIG. 23. In this example, intraoperative landmark point 3248' is in the same grid location as intraoperative landmark point 3248, FIG. 22. A vector can then be calculated from intraop landmark point 3248' to corrected point 3208' using calculations similar to that described above in relation to FIG. 21. In this construction, a "Details" window 3270 graphically shows the change in position of initial preop landmark point 3208 to corrected landmark point 3208'.

Other alternative constructions will change the order of various steps, including the generation of various digital landmarks. An additional alternative construction will identify an estimated center of rotation in the preop image instead of the intraop image, using a similar digital circle placed around the femoral head, or similar technique to annotate the estimate center of rotation.

Although specific features of the present invention are shown in some drawings and not in others, this is for convenience only, as each feature may be combined with any or all of the other features in accordance with the invention. While there have been shown, described, and pointed out fundamental novel features of the invention as applied to one or more preferred embodiments thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated.

It is also to be understood that the drawings are not necessarily drawn to scale, but that they are merely conceptual in nature. Other embodiments will occur to those skilled in the art and are within the scope of the present disclosure.

The invention claimed is:

1. A method comprising:
  acquiring a preoperative image of a patient's hip joint, the preoperative image depicting at least (i) a femoral feature point on a femur of the patient and (ii) a plurality of pelvic feature points on a pelvis of the patient,
  acquiring an intraoperative image depicting at least (i) the femoral feature point on the patient's femur, (ii) the plurality of pelvic feature points on the patient's pelvis, and (iii) a trial prosthesis positioned in the patient's hip joint,
  digitally registering the femoral feature point in the preoperative image,
  digitally registering a longitudinal axis of the patient's femur in the preoperative image,
  digitally registering the plurality of pelvic feature points in the preoperative image,
  digitally registering the femoral feature point in the intraoperative image,
  digitally registering the longitudinal axis of the patient's femur in the intraoperative image,
  digitally registering the plurality of pelvic feature points in the intraoperative image,
  digitally registering a center of rotation in the intraoperative image,
  determining an angular difference between (i) a preoperative orientation of the digitally registered longitudinal axis in the preoperative image relative to the digitally registered plurality of pelvic feature points in the preoperative image and (ii) an intraoperative orientation of the digitally registered longitudinal axis in the intraoperative image relative to the digitally registered plurality of pelvic feature points in the intraoperative image,
  determining a corrected femoral feature point in the intraoperative image using the digitally registered femoral feature point in the intraoperative image, the digitally registered center of rotation in the intraoperative image, and the determined angular difference,
  predicting a post-operative leg length differential, offset, or both using a positional difference between (i) a preoperative location of the digitally registered femoral feature point in the preoperative image relative to the digitally registered plurality of pelvic feature points in the preoperative image and (ii) an intraoperative location of the corrected femoral feature point in the intraoperative image relative to the digitally registered plurality of pelvic feature points in the intraoperative image,
  displaying the predicted post-operative leg length differential, offset, or both to a surgeon operating on the patient's hip joint,
  selecting a final prosthesis to be implanted in the patient's hip joint based on the predicted post-operative leg length differential, offset, or both, and
  implanting the final prosthesis in the patient's hip joint.

2. The method of claim 1, wherein selecting the final prosthesis to be implanted in the patient's hip joint comprises selecting a final prosthesis that is the same size as the trial prosthesis.

3. The method of claim 1, wherein selecting the final prosthesis to be implanted in the patient's hip joint comprises selecting a final prosthesis that is a different size than the trial prosthesis.

4. The method of claim 1, wherein digitally registering the longitudinal axis in the intraoperative image comprises aligning a digital template over a femoral component of the prosthesis depicted in the intraoperative image.

5. The method of claim 4, wherein digitally registering the longitudinal axis in the preoperative image comprises aligning the digital template over a medullary canal of the patient's femur depicted in the preoperative image.

6. The method of claim 1, wherein:
  digitally registering the plurality of pelvic feature points in the preoperative image comprises positioning a line that connects a pubic symphysis point in the preoperative image to an anterior superior iliac spine point in the preoperative image, and
  digitally registering the plurality of pelvic feature points in the intraoperative image comprises positioning a line that connects the pubic symphysis point in the intraoperative image to the anterior superior iliac spine point in the intraoperative image.

7. The method of claim 6, wherein:
  digitally registering the plurality of pelvic feature points in the preoperative image further comprises digitally registering a pelvic tear drop point in the preoperative image, and
  digitally registering the plurality of pelvic feature points in the intraoperative image further comprises digitally registering the pelvic tear drop point in the intraoperative image.

8. The method of claim 1, wherein digitally registering the center of rotation in the intraoperative image comprises positioning a circle around an acetabular cup of the prosthesis depicted in the intraoperative image.

9. The method of claim 1, wherein digitally registering the center of rotation in the intraoperative image comprises aligning a digital template over an acetabular cup of the prosthesis depicted in the intraoperative image.

10. The method of claim 1, further comprising aligning the preoperative image and the intraoperative image using the digitally registered pluralities of pelvic feature points, prior to determining the positional difference.

11. The method of claim 10, wherein aligning the preoperative image and the intraoperative image comprises rescaling at least one of the preoperative image or the intraoperative image.

12. The method of claim 10, wherein determining the angular difference comprises calculating an angle between the digitally registered longitudinal axis in the preoperative image and the digitally registered longitudinal axis in the intraoperative image, after the preoperative image and the intraoperative image have been aligned using the digitally registered pluralities of pelvic feature points.

13. The method of claim 1, wherein determining the angular difference comprises:
superimposing the preoperative image and the intraoperative image such that the digitally registered femoral feature point in the preoperative image and the digitally registered femoral feature point in the intraoperative image are aligned, and
rotating the preoperative image or the intraoperative image about the femoral feature point until the patient's femur in the preoperative image and the patient's femur in the intraoperative image are aligned.

14. The method of claim 13, wherein the femoral feature point is located on a greater trochanter of the patient's femur.

15. The method of claim 13, wherein determining the angular difference further comprises adjusting a transparency of at least one of the preoperative image or the intraoperative image.

16. The method of claim 13, wherein determining the angular difference further comprises recording, as the angular difference, an amount that the preoperative image or the intraoperative image was rotated to align the patient's femur in the preoperative image and the patient's femur in the intraoperative image.

17. The method of claim 13, wherein determining the angular difference further comprises, after the patient's femur in the preoperative image and the patient's femur in the intraoperative image have been aligned, determining a rotational displacement between the digitally registered plurality of pelvic feature points in the preoperative image and the digitally registered plurality of pelvic feature points in the intraoperative image.

18. One or more non-transitory computer-readable media storing instructions that, when executed by a processor, cause the processor to:
acquire a preoperative image of a patient's hip joint, the preoperative image depicting at least (i) a femoral feature point on a femur of the patient and (ii) a plurality of pelvic feature points on a pelvis of the patient,
acquire an intraoperative image depicting at least (i) the femoral feature point on the patient's femur, (ii) the plurality of pelvic feature points on the patient's pelvis, and (iii) a trial prosthesis inserted in the patient's hip joint,
digitally register the femoral feature point in the preoperative image,
digitally register a longitudinal axis of the patient's femur in the preoperative image,
digitally register the plurality of pelvic feature points in the preoperative image,
digitally register the femoral feature point in the intraoperative image,
digitally register the longitudinal axis of the patient's femur in the intraoperative image,
digitally register the plurality of pelvic feature points in the intraoperative image,
digitally register a center of rotation in the intraoperative image,
determine an angular difference between (i) a preoperative orientation of the digitally registered longitudinal axis in the preoperative image relative to the digitally registered plurality of pelvic feature points in the preoperative image and (ii) an intraoperative orientation of the digitally registered longitudinal axis in the intraoperative image relative to the digitally registered plurality of pelvic feature points in the intraoperative image,
determine a corrected femoral feature point in the intraoperative image using the digitally registered femoral feature point in the intraoperative image, the digitally registered center of rotation in the intraoperative image, and the determined angular difference,
predict a post-operative leg length differential, offset, or both using a positional difference between (i) a preoperative location of the digitally registered femoral feature point in the preoperative image relative to the digitally registered plurality of pelvic feature points in the preoperative image and (ii) an intraoperative location of the corrected femoral feature point in the intraoperative image relative to the digitally registered plurality of pelvic feature points in the intraoperative image,
initiate display of the predicted post-operative leg length differential, offset, or both to a surgeon operating on the patient's hip joint,
receive an input indicating the surgeon's selection of a final prosthesis in response to the predicted post-operative leg length differential, offset, or both, and
initiate display of guidance for the surgeon to implant the final prosthesis in the patient's hip joint in response to the input.

19. The one or more non-transitory computer-readable media of claim 18, wherein the instructions, when executed by the processor, cause the processor to determine the angular difference by:
superimposing the preoperative image and the intraoperative image such that the digitally registered femoral feature point in the preoperative image and the digitally registered femoral feature point in the intraoperative image are aligned, and
recording, as the angular difference, an amount that the preoperative image or the intraoperative image is rotated in order to align the patient's femur in the preoperative image and the patient's femur in the intraoperative image.

20. The one or more non-transitory computer-readable media of claim 18, wherein the instructions, when executed by the processor, cause the processor to determine the angular difference by determining a rotational displacement between the digitally registered plurality of pelvic feature points in the preoperative image and the digitally registered plurality of pelvic feature points in the intraoperative image, after the digitally registered longitudinal axis in the preoperative image and the digitally registered longitudinal axis in the intraoperative image have been aligned.

* * * * *